United States Patent
Künkel et al.

(10) Patent No.: US 7,556,937 B2
(45) Date of Patent: Jul. 7, 2009

(54) METHOD FOR PRODUCING ERGOSTA-5,7-DIENOL AND/OR BIOSYNTHETIC INTERMEDIATE AND/OR SECONDARY PRODUCTS THEREOF IN TRANSGENIC ORGANISMS

(75) Inventors: Andreas Künkel, Neustadt (DE); Markus Veen, Berlin (DE); Christine Lang, Berlin (DE)

(73) Assignee: OrganoBalance GmbH, Berlin (DE)

( * ) Notice: Subject to any disclaimer, the term of this patent is extended or adjusted under 35 U.S.C. 154(b) by 0 days.

(21) Appl. No.: 10/549,871

(22) PCT Filed: Mar. 12, 2004

(86) PCT No.: PCT/EP2004/002582

§ 371 (c)(1),
(2), (4) Date: Sep. 16, 2005

(87) PCT Pub. No.: WO2004/083407

PCT Pub. Date: Sep. 30, 2004

(65) Prior Publication Data

US 2006/0269986 A1    Nov. 30, 2006

(30) Foreign Application Priority Data

Mar. 19, 2003    (DE) ............................... 103 12 314

(51) Int. Cl.
*C12P 33/00* (2006.01)
*C12N 9/02* (2006.01)
(52) U.S. Cl. ........................................ 435/52; 435/189
(58) Field of Classification Search .................... 435/52, 435/189
See application file for complete search history.

(56) References Cited

FOREIGN PATENT DOCUMENTS

| CA | 2 305 780 A1 | 4/1999 |
|---|---|---|
| DE | 197 44 212 | 4/1999 |
| EP | 0 486 290 A2 | 5/1992 |
| WO | WO-02/061072 A2 | 8/2002 |
| WO | WO-03/064650 A1 | 8/2003 |

OTHER PUBLICATIONS

Basson, M. et al., "Structural and Functional Conservation Between Yeast and Human 3-Hydroxy-3-Methylglutaryl Co-enzyme A Reductases, The Rate-Limiting Enzyme of Sterol Biosynthesis", Molecular and Cellular Biology 8 (1988), pp. 3797-3808.
Polakowski, T. et al., "Overexpression of a Cytosolic Hydroxymethylglutaryl-CoA Reductase Leads to Squalene Accumulation in Yeast", Appl. Microbiol. Biotechnol. 49 (1998), pp. 66-71.
Kalb, V.F. et al., "Isolation of a Cytochrome P-450 Structural Gene from *Saccharomyces cerevisiae*", Gene 45 (1986), pp. 237-245.
Jandrositz, A. et al., "The Gene Encoding Squalene Epoxidase from *Saccharomyces cerevisiae*: Cloning and Characterization", Gene 107 (1991), pp. 155-160.
Jennings, S. et al., "Molecular Cloning and Characterization of the Yeast Gene for Squalene Synthetase", Proc. Natl. Acad. Sci. USA 88 (1991), pp. 6038-6042.
Tainaka, H. et al., "Effects of Elevated Expression of the $CYP51$ ($P450_{14DM}$) Gene on the Sterol Contents of *Saccharomyces cerevisiae*", Journal of Fermentation and Bioengineering 79 (1995), pp. 64-66.
Polakowski, T., "Molekularbiologische Beeinflussung des Ergosterolstoffwechsels der Hefe *Saccharomyces cerevisiae*", Shaker Verlag Aachen, Dissertation, Technischen Universität Berlin, Germany, 1999, pp. 59-66.
Pena-Diaz, J. et al., "A soluble 3-hydroxy-3-methylglutaryl-CoA reductase in the protozoan Trypanosoma cruzi", Biochem. J., (1997), vol. 324, pp. 619-626.
Favre, B. et al., "Characterization of Squalene Epoxidase Activity from the Dermatophyte Trichophyton rubrum and its Inhibition by Terbinafine and Other Antimycotic Agents", Antimicrobial Agents and Chemotherapy, Feb. 1996, vol. 40, No. 2, pp. 443-447.
Robinson, G.W. et al., "Conservation between Human and Fungal Squalene Synthetases: Similarities in Structure, Function, and Regulation", Molecular and Cellular Biology, May 1993, vol. 13, No. 5, pp. 2706-2717.
Georgopapadakou, N.H. et al., "Effects of Squalene Epoxidase Inhibitors on Candida albicans", Antimicrobial Agents and Chemotherapy, Aug. 1992, vol. 36, No. 8, pp. 1779-1781.
Jennings, S.M. et al., "Molecular cloning and characterization of the yeast gene for squalene synthetase", Proc. Natl. Acad. Sci. USA, Jul. 1991, vol. 88, pp. 6038-6042.
Nagumo, A. et al., "Purification and chacterization of recombinant squalene epoxidase", Journal of Lipid Research, 1995, vol. 36, pp. 1489-1497.
Tai, H.H. et al., "Squalene Epoxidase of Rat Liver", The Journal of Biological Chemistry, Jun. 25, 1972, vol. 247, No. 12 pp. 3767-3773.
Basson, M.E. et al., "Structural and Functional Conservation between Yeast and Human 3-Hydroxy-3-Methylglutaryl Coenzyme A Reductases, the Rate-Limiting Enzyme of Sterol Biosynthesis", Molecular and Cellular Biology, Sep. 1988, vol. 8, No. 9, pp. 3797-3808.
Jandrositz, A. et al., "The gene encoding squalene epoxidase from *Saccharomyces cerevisiae*: cloning and characterization", 1991, vol. 107, pp. 155-160.

(Continued)

*Primary Examiner*—Tekchand Saidha
(74) *Attorney, Agent, or Firm*—Mayer & Williams PC; Ann Wieczorek, Esq.; Keum J. Park, Esq.

(57) ABSTRACT

The present invention relates to a method for the production of ergosta-5,7-dienol and/or its biosynthetic intermediates and/or metabolites by culturing genetically modified organisms, and to the genetically modified organisms, in particular yeasts, themselves.

14 Claims, 2 Drawing Sheets

OTHER PUBLICATIONS

Bischoff, K.M. et al., "3-Hydroxy-3-Methylglutaryl-Coenzyme A Reductase from Haloferax volcanii: Purification, Characterization, and Expression in *Escherichia coli*", Journal of Bacteriology, Jan. 1996, vol. 178., No. 1, pp. 19-23.

Bochar, D.A. et al., "3-Hydroxy-3-Methylglutaryl Coenzyme A Reductase of Sulfolobus solfataricus: DNA Sequence, Phylogeny, Expression in *Escherichia coli* of the hmgA Gene, and Purification and Kinetic Characterization of the Gene Product", Journal of Bacteriology, Jun. 1997, vol. 179, No. 11, pp. 3632-3638.

Nakamura, Yuichi et al., "Transcriptional Regulation of Squalene Epoxidase by Sterols and Inhibitors in HeLa Cells," The Journal of Biological Chemistry, vol. 271, No. 14, Issue of Apr. 5, 1996, pp. 8053-8056.

SEQUENCE LISTING

<160> NUMBER OF SEQ ID NOS: 14

<210> SEQ ID NO 1
<211> LENGTH: 1617
<212> TYPE: DNA

-continued

<213> ORGANISM: Saccharomyces cerevisiae
<220> FEATURE:
<221> NAME/KEY: CDS
<222> LOCATION: (1)..(1617)

<400> SEQUENCE: 1

| | | | | | | | | | | | | | | | | |
|---|---|---|---|---|---|---|---|---|---|---|---|---|---|---|---|---|
| atg | agt | tct | gtc | gca | gaa | aat | ata | ata | caa | cat | gcc | act | cat | aat | tct | 48 |
| Met | Ser | Ser | Val | Ala | Glu | Asn | Ile | Ile | Gln | His | Ala | Thr | His | Asn | Ser | |
| 1 | | | | 5 | | | | | 10 | | | | | 15 | | |
| acg | cta | cac | caa | ttg | gct | aaa | gac | cag | ccc | tct | gta | ggc | gtc | act | act | 96 |
| Thr | Leu | His | Gln | Leu | Ala | Lys | Asp | Gln | Pro | Ser | Val | Gly | Val | Thr | Thr | |
| | | | 20 | | | | | 25 | | | | | 30 | | | |
| gcc | ttc | agt | atc | ctg | gat | aca | ctt | aag | tct | atg | tca | tat | ttg | aaa | ata | 144 |
| Ala | Phe | Ser | Ile | Leu | Asp | Thr | Leu | Lys | Ser | Met | Ser | Tyr | Leu | Lys | Ile | |
| | | 35 | | | | | 40 | | | | | 45 | | | | |
| ttt | gct | act | tta | atc | tgt | att | ctt | ttg | gtt | tgg | gac | caa | gtt | gca | tat | 192 |
| Phe | Ala | Thr | Leu | Ile | Cys | Ile | Leu | Leu | Val | Trp | Asp | Gln | Val | Ala | Tyr | |
| | 50 | | | | | 55 | | | | | 60 | | | | | |
| caa | atc | aag | aaa | ggt | tcc | atc | gca | ggt | cca | aag | ttt | aag | ttc | tgg | ccc | 240 |
| Gln | Ile | Lys | Lys | Gly | Ser | Ile | Ala | Gly | Pro | Lys | Phe | Lys | Phe | Trp | Pro | |
| 65 | | | | | 70 | | | | | 75 | | | | | 80 | |
| atc | atc | ggt | cca | ttt | ttg | gaa | tcc | tta | gat | cca | aag | ttt | gaa | gaa | tat | 288 |
| Ile | Ile | Gly | Pro | Phe | Leu | Glu | Ser | Leu | Asp | Pro | Lys | Phe | Glu | Glu | Tyr | |
| | | | | 85 | | | | | 90 | | | | | 95 | | |
| aag | gct | aag | tgg | gca | tcc | ggt | cca | ctt | tca | tgt | gtt | tct | att | ttc | cat | 336 |
| Lys | Ala | Lys | Trp | Ala | Ser | Gly | Pro | Leu | Ser | Cys | Val | Ser | Ile | Phe | His | |
| | | | 100 | | | | | 105 | | | | | 110 | | | |
| aaa | ttt | gtt | gtt | atc | gca | tct | act | aga | gac | ttg | gca | aga | aag | atc | ttg | 384 |
| Lys | Phe | Val | Val | Ile | Ala | Ser | Thr | Arg | Asp | Leu | Ala | Arg | Lys | Ile | Leu | |
| | | 115 | | | | | 120 | | | | | 125 | | | | |
| caa | tct | tcc | aaa | ttc | gtc | aaa | cct | tgc | gtt | gtc | gat | gtt | gct | gtg | aag | 432 |
| Gln | Ser | Ser | Lys | Phe | Val | Lys | Pro | Cys | Val | Val | Asp | Val | Ala | Val | Lys | |
| | 130 | | | | | 135 | | | | | 140 | | | | | |
| atc | tta | aga | cct | tgc | aat | tgg | gtt | ttt | ttg | gac | ggt | aaa | gct | cat | act | 480 |
| Ile | Leu | Arg | Pro | Cys | Asn | Trp | Val | Phe | Leu | Asp | Gly | Lys | Ala | His | Thr | |
| 145 | | | | | 150 | | | | | 155 | | | | | 160 | |
| gat | tac | aga | aaa | tca | tta | aac | ggt | ctt | ttc | act | aaa | caa | gct | ttg | gct | 528 |
| Asp | Tyr | Arg | Lys | Ser | Leu | Asn | Gly | Leu | Phe | Thr | Lys | Gln | Ala | Leu | Ala | |
| | | | | 165 | | | | | 170 | | | | | 175 | | |
| caa | tac | tta | cct | tca | ttg | gaa | caa | atc | atg | gat | aag | tac | atg | gat | aag | 576 |
| Gln | Tyr | Leu | Pro | Ser | Leu | Glu | Gln | Ile | Met | Asp | Lys | Tyr | Met | Asp | Lys | |
| | | | 180 | | | | | 185 | | | | | 190 | | | |
| ttt | gtt | cgt | tta | tct | aag | gag | aat | aac | tac | gag | ccc | cag | gtc | ttt | ttc | 624 |
| Phe | Val | Arg | Leu | Ser | Lys | Glu | Asn | Asn | Tyr | Glu | Pro | Gln | Val | Phe | Phe | |
| | | 195 | | | | | 200 | | | | | 205 | | | | |
| cat | gaa | atg | aga | gaa | att | ctt | tgc | gcc | tta | tca | ttg | aac | tct | ttc | tgt | 672 |
| His | Glu | Met | Arg | Glu | Ile | Leu | Cys | Ala | Leu | Ser | Leu | Asn | Ser | Phe | Cys | |
| | 210 | | | | | 215 | | | | | 220 | | | | | |
| ggt | aac | tat | att | acc | gaa | gat | caa | gtc | aga | aag | att | gct | gat | gat | tac | 720 |
| Gly | Asn | Tyr | Ile | Thr | Glu | Asp | Gln | Val | Arg | Lys | Ile | Ala | Asp | Asp | Tyr | |
| 225 | | | | | 230 | | | | | 235 | | | | | 240 | |
| tat | ttg | gtt | aca | gca | gca | ttg | gaa | tta | gtc | aac | ttc | cca | att | att | atc | 768 |
| Tyr | Leu | Val | Thr | Ala | Ala | Leu | Glu | Leu | Val | Asn | Phe | Pro | Ile | Ile | Ile | |
| | | | | 245 | | | | | 250 | | | | | 255 | | |
| cct | tac | act | aaa | aca | tgg | tat | ggt | aag | aaa | act | gca | gac | atg | gcc | atg | 816 |
| Pro | Tyr | Thr | Lys | Thr | Trp | Tyr | Gly | Lys | Lys | Thr | Ala | Asp | Met | Ala | Met | |
| | | | 260 | | | | | 265 | | | | | 270 | | | |
| aag | att | ttc | gaa | aac | tgt | gct | caa | atg | gct | aag | gat | cat | att | gct | gca | 864 |
| Lys | Ile | Phe | Glu | Asn | Cys | Ala | Gln | Met | Ala | Lys | Asp | His | Ile | Ala | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| ggt | ggt | aag | cca | gtt | tgt | gtt | atg | gat | gct | tgg | tgt | aag | ttg | atg | cac | 912 |
| Gly | Gly | Lys | Pro | Val | Cys | Val | Met | Asp | Ala | Trp | Cys | Lys | Leu | Met | His | |
| | 290 | | | | 295 | | | | | 300 | | | | | | |
| gat | gca | aag | aat | agt | aac | gat | gat | gat | tct | aga | atc | tac | cac | aga | gag | 960 |
| Asp | Ala | Lys | Asn | Ser | Asn | Asp | Asp | Asp | Ser | Arg | Ile | Tyr | His | Arg | Glu | |
| 305 | | | | | 310 | | | | | 315 | | | | | 320 | |
| ttt | act | aac | aag | gaa | atc | tcc | gaa | gct | gtt | ttc | act | ttc | tta | ttt | gct | 1008 |
| Phe | Thr | Asn | Lys | Glu | Ile | Ser | Glu | Ala | Val | Phe | Thr | Phe | Leu | Phe | Ala | |
| | | | | 325 | | | | | 330 | | | | | 335 | | |
| tct | caa | gat | gcc | tct | tct | tct | tta | gct | tgt | tgg | ttg | ttc | caa | att | gtt | 1056 |
| Ser | Gln | Asp | Ala | Ser | Ser | Ser | Leu | Ala | Cys | Trp | Leu | Phe | Gln | Ile | Val | |
| | | | 340 | | | | | 345 | | | | | 350 | | | |
| gct | gac | cgt | cca | gat | gtc | tta | gct | aag | atc | aga | gaa | gaa | caa | ttg | gct | 1104 |
| Ala | Asp | Arg | Pro | Asp | Val | Leu | Ala | Lys | Ile | Arg | Glu | Glu | Gln | Leu | Ala | |
| | | 355 | | | | | 360 | | | | | 365 | | | | |
| gtt | cgt | aac | aat | gac | atg | tct | acc | gaa | ttg | aac | ttg | gat | ttg | att | gag | 1152 |
| Val | Arg | Asn | Asn | Asp | Met | Ser | Thr | Glu | Leu | Asn | Leu | Asp | Leu | Ile | Glu | |
| 370 | | | | | 375 | | | | | 380 | | | | | | |
| aaa | atg | aag | tac | acc | aat | atg | gtc | ata | aaa | gaa | act | ttg | cgt | tac | aga | 1200 |
| Lys | Met | Lys | Tyr | Thr | Asn | Met | Val | Ile | Lys | Glu | Thr | Leu | Arg | Tyr | Arg | |
| 385 | | | | | 390 | | | | | 395 | | | | | 400 | |
| cct | cct | gtc | ttg | atg | gtt | cca | tat | gtt | gtt | aag | aag | aat | ttc | cca | gtt | 1248 |
| Pro | Pro | Val | Leu | Met | Val | Pro | Tyr | Val | Val | Lys | Lys | Asn | Phe | Pro | Val | |
| | | | | 405 | | | | | 410 | | | | | 415 | | |
| tcc | cct | aac | tat | acc | gca | cca | aag | ggc | gct | atg | tta | att | cca | acc | tta | 1296 |
| Ser | Pro | Asn | Tyr | Thr | Ala | Pro | Lys | Gly | Ala | Met | Leu | Ile | Pro | Thr | Leu | |
| | | | 420 | | | | | 425 | | | | | 430 | | | |
| tac | cca | gct | tta | cat | gat | cct | gaa | gtt | tac | gaa | aat | cct | gat | gag | ttc | 1344 |
| Tyr | Pro | Ala | Leu | His | Asp | Pro | Glu | Val | Tyr | Glu | Asn | Pro | Asp | Glu | Phe | |
| | | 435 | | | | | 440 | | | | | 445 | | | | |
| atc | cct | gaa | aga | tgg | gta | gaa | ggc | tct | aag | gct | agt | gaa | gca | aag | aag | 1392 |
| Ile | Pro | Glu | Arg | Trp | Val | Glu | Gly | Ser | Lys | Ala | Ser | Glu | Ala | Lys | Lys | |
| | 450 | | | | | 455 | | | | | 460 | | | | | |
| aat | tgg | ttg | gtt | ttt | ggt | tgt | ggt | cca | cac | gtt | tgc | tta | ggt | caa | aca | 1440 |
| Asn | Trp | Leu | Val | Phe | Gly | Cys | Gly | Pro | His | Val | Cys | Leu | Gly | Gln | Thr | |
| 465 | | | | | 470 | | | | | 475 | | | | | 480 | |
| tat | gtc | atg | att | acc | ttc | gcc | gct | ttg | ttg | ggt | aaa | ttt | gca | cta | tat | 1488 |
| Tyr | Val | Met | Ile | Thr | Phe | Ala | Ala | Leu | Leu | Gly | Lys | Phe | Ala | Leu | Tyr | |
| | | | | 485 | | | | | 490 | | | | | 495 | | |
| act | gat | ttc | cat | cat | aca | gtg | act | cca | tta | agt | gaa | aaa | atc | aag | gtt | 1536 |
| Thr | Asp | Phe | His | His | Thr | Val | Thr | Pro | Leu | Ser | Glu | Lys | Ile | Lys | Val | |
| | | | 500 | | | | | 505 | | | | | 510 | | | |
| ttc | gct | aca | att | ttc | cca | aaa | gat | gat | ttg | tta | ctg | act | ttc | aaa | aag | 1584 |
| Phe | Ala | Thr | Ile | Phe | Pro | Lys | Asp | Asp | Leu | Leu | Leu | Thr | Phe | Lys | Lys | |
| | | 515 | | | | | 520 | | | | | 525 | | | | |
| aga | gac | cca | att | act | gga | gaa | gtc | ttc | gaa | taa | | | | | | 1617 |
| Arg | Asp | Pro | Ile | Thr | Gly | Glu | Val | Phe | Glu | | | | | | | |
| | 530 | | | | | 535 | | | | | | | | | | |

<210> SEQ ID NO 2
<211> LENGTH: 538
<212> TYPE: PRT
<213> ORGANISM: Saccharomyces cerevisiae

<400> SEQUENCE: 2

Met Ser Ser Val Ala Glu Asn Ile Ile Gln His Ala Thr His Asn Ser
1               5                   10                  15

Thr Leu His Gln Leu Ala Lys Asp Gln Pro Ser Val Gly Val Thr Thr
            20                  25                  30

Ala Phe Ser Ile Leu Asp Thr Leu Lys Ser Met Ser Tyr Leu Lys Ile

-continued

```
                35                  40                  45
Phe Ala Thr Leu Ile Cys Ile Leu Leu Val Trp Asp Gln Val Ala Tyr
 50                  55                  60
Gln Ile Lys Lys Gly Ser Ile Ala Gly Pro Lys Phe Lys Phe Trp Pro
 65                  70                  75                  80
Ile Ile Gly Pro Phe Leu Glu Ser Leu Asp Pro Lys Phe Glu Glu Tyr
                 85                  90                  95
Lys Ala Lys Trp Ala Ser Gly Pro Leu Ser Cys Val Ser Ile Phe His
                100                 105                 110
Lys Phe Val Val Ile Ala Ser Thr Arg Asp Leu Ala Arg Lys Ile Leu
                115                 120                 125
Gln Ser Ser Lys Phe Val Lys Pro Cys Val Val Asp Val Ala Val Lys
130                 135                 140
Ile Leu Arg Pro Cys Asn Trp Val Phe Leu Asp Gly Lys Ala His Thr
145                 150                 155                 160
Asp Tyr Arg Lys Ser Leu Asn Gly Leu Phe Thr Lys Gln Ala Leu Ala
                165                 170                 175
Gln Tyr Leu Pro Ser Leu Glu Gln Ile Met Asp Lys Tyr Met Asp Lys
                180                 185                 190
Phe Val Arg Leu Ser Lys Glu Asn Asn Tyr Glu Pro Gln Val Phe Phe
                195                 200                 205
His Glu Met Arg Glu Ile Leu Cys Ala Leu Ser Leu Asn Ser Phe Cys
210                 215                 220
Gly Asn Tyr Ile Thr Glu Asp Gln Val Arg Lys Ile Ala Asp Asp Tyr
225                 230                 235                 240
Tyr Leu Val Thr Ala Ala Leu Glu Leu Val Asn Phe Pro Ile Ile Ile
                245                 250                 255
Pro Tyr Thr Lys Thr Trp Tyr Gly Lys Lys Thr Ala Asp Met Ala Met
                260                 265                 270
Lys Ile Phe Glu Asn Cys Ala Gln Met Ala Lys Asp His Ile Ala Ala
                275                 280                 285
Gly Gly Lys Pro Val Cys Val Met Asp Ala Trp Cys Lys Leu Met His
290                 295                 300
Asp Ala Lys Asn Ser Asn Asp Asp Ser Arg Ile Tyr His Arg Glu
305                 310                 315                 320
Phe Thr Asn Lys Glu Ile Ser Glu Ala Val Phe Thr Phe Leu Phe Ala
                325                 330                 335
Ser Gln Asp Ala Ser Ser Leu Ala Cys Trp Leu Phe Gln Ile Val
                340                 345                 350
Ala Asp Arg Pro Asp Val Leu Ala Lys Ile Arg Glu Glu Gln Leu Ala
                355                 360                 365
Val Arg Asn Asn Asp Met Ser Thr Glu Leu Asn Leu Asp Leu Ile Glu
                370                 375                 380
Lys Met Lys Tyr Thr Asn Met Val Ile Lys Glu Thr Leu Arg Tyr Arg
385                 390                 395                 400
Pro Pro Val Leu Met Val Pro Tyr Val Lys Lys Asn Phe Pro Val
                405                 410                 415
Ser Pro Asn Tyr Thr Ala Pro Lys Gly Ala Met Leu Ile Pro Thr Leu
                420                 425                 430
Tyr Pro Ala Leu His Asp Pro Glu Val Tyr Glu Asn Pro Asp Glu Phe
                435                 440                 445
Ile Pro Glu Arg Trp Val Glu Gly Ser Lys Ala Ser Glu Ala Lys Lys
450                 455                 460
```

```
Asn Trp Leu Val Phe Gly Cys Gly Pro His Val Cys Leu Gly Gln Thr
465                 470                 475                 480

Tyr Val Met Ile Thr Phe Ala Ala Leu Leu Gly Lys Phe Ala Leu Tyr
                485                 490                 495

Thr Asp Phe His His Thr Val Thr Pro Leu Ser Glu Lys Ile Lys Val
            500                 505                 510

Phe Ala Thr Ile Phe Pro Lys Asp Leu Leu Leu Thr Phe Lys Lys
        515                 520                 525

Arg Asp Pro Ile Thr Gly Glu Val Phe Glu
    530                 535

<210> SEQ ID NO 3
<211> LENGTH: 1578
<212> TYPE: DNA
<213> ORGANISM: Artificial sequence
<220> FEATURE:
<223> OTHER INFORMATION: Description of synthetic sequence: truncated
      HMG
<220> FEATURE:
<221> NAME/KEY: misc_feature
<222> LOCATION: (1)..(1578)
<223> OTHER INFORMATION: CDS

<400> SEQUENCE: 3 atg gac caa ttg gtg aaa act gaa gtc acc aag aag tct ttt act gct     48
Met Asp Gln Leu Val Lys Thr Glu Val Thr Lys Lys Ser Phe Thr Ala
1               5                   10                  15 cct gta caa aag gct tct aca cca gtt tta acc aat aaa aca gtc att     96
Pro Val Gln Lys Ala Ser Thr Pro Val Leu Thr Asn Lys Thr Val Ile
            20                  25                  30 tct gga tcg aaa gtc aaa agt tta tca tct gcg caa tcg agc tca tca    144
Ser Gly Ser Lys Val Lys Ser Leu Ser Ser Ala Gln Ser Ser Ser Ser
        35                  40                  45 gga cct tca tca tct agt gag gaa gat gat tcc cgc gat att gaa agc    192
Gly Pro Ser Ser Ser Ser Glu Glu Asp Asp Ser Arg Asp Ile Glu Ser
    50                  55                  60 ttg gat aag aaa ata cgt cct tta gaa gaa tta gaa gca tta tta agt    240
Leu Asp Lys Lys Ile Arg Pro Leu Glu Glu Leu Glu Ala Leu Leu Ser
65                  70                  75                  80 agt gga aat aca aaa caa ttg aag aac aaa gag gtc gct gcc ttg gtt    288
Ser Gly Asn Thr Lys Gln Leu Lys Asn Lys Glu Val Ala Ala Leu Val
                85                  90                  95 att cac ggt aag tta cct ttg tac gct ttg gag aaa aaa tta ggt gat    336
Ile His Gly Lys Leu Pro Leu Tyr Ala Leu Glu Lys Lys Leu Gly Asp
            100                 105                 110 act acg aga gcg gtt gcg gta cgt agg aag gct ctt tca att ttg gca    384
Thr Thr Arg Ala Val Ala Val Arg Arg Lys Ala Leu Ser Ile Leu Ala
        115                 120                 125 gaa gct cct gta tta gca tct gat cgt tta cca tat aaa aat tat gac    432
Glu Ala Pro Val Leu Ala Ser Asp Arg Leu Pro Tyr Lys Asn Tyr Asp
    130                 135                 140 tac gac cgc gta ttt ggc gct tgt tgt gaa aat gtt ata ggt tac atg    480
Tyr Asp Arg Val Phe Gly Ala Cys Cys Glu Asn Val Ile Gly Tyr Met
145                 150                 155                 160 cct ttg ccc gtt ggt gtt ata ggc ccc ttg gtt atc gat ggt aca tct    528
Pro Leu Pro Val Gly Val Ile Gly Pro Leu Val Ile Asp Gly Thr Ser
                165                 170                 175 tat cat ata cca atg gca act aca gag ggt tgt ttg gta gct tct gcc    576
Tyr His Ile Pro Met Ala Thr Thr Glu Gly Cys Leu Val Ala Ser Ala
            180                 185                 190
```

-continued

| | | |
|---|---|---|
| atg cgt ggc tgt aag gca atc aat gct ggc ggt ggt gca aca act gtt<br>Met Arg Gly Cys Lys Ala Ile Asn Ala Gly Gly Gly Ala Thr Thr Val<br>195 200 205 | | 624 |
| tta act aag gat ggt atg aca aga ggc cca gta gtc cgt ttc cca act<br>Leu Thr Lys Asp Gly Met Thr Arg Gly Pro Val Val Arg Phe Pro Thr<br>210 215 220 | | 672 |
| ttg aaa aga tct ggt gcc tgt aag ata tgg tta gac tca gaa gag gga<br>Leu Lys Arg Ser Gly Ala Cys Lys Ile Trp Leu Asp Ser Glu Glu Gly<br>225 230 235 240 | | 720 |
| caa aac gca att aaa aaa gct ttt aac tct aca tca aga ttt gca cgt<br>Gln Asn Ala Ile Lys Lys Ala Phe Asn Ser Thr Ser Arg Phe Ala Arg<br>245 250 255 | | 768 |
| ctg caa cat att caa act tgt cta gca gga gat tta ctc ttc atg aga<br>Leu Gln His Ile Gln Thr Cys Leu Ala Gly Asp Leu Leu Phe Met Arg<br>260 265 270 | | 816 |
| ttt aga aca act act ggt gac gca atg ggt atg aat atg att tct aaa<br>Phe Arg Thr Thr Thr Gly Asp Ala Met Gly Met Asn Met Ile Ser Lys<br>275 280 285 | | 864 |
| ggt gtc gaa tac tca tta aag caa atg gta gaa gag tat ggc tgg gaa<br>Gly Val Glu Tyr Ser Leu Lys Gln Met Val Glu Glu Tyr Gly Trp Glu<br>290 295 300 | | 912 |
| gat atg gag gtt gtc tcc gtt tct ggt aac tac tgt acc gac aaa aaa<br>Asp Met Glu Val Val Ser Val Ser Gly Asn Tyr Cys Thr Asp Lys Lys<br>305 310 315 320 | | 960 |
| cca gct gcc atc aac tgg atc gaa ggt cgt ggt aag agt gtc gtc gca<br>Pro Ala Ala Ile Asn Trp Ile Glu Gly Arg Gly Lys Ser Val Val Ala<br>325 330 335 | | 1008 |
| gaa gct act att cct ggt gat gtt gtc aga aaa gtg tta aaa agt gat<br>Glu Ala Thr Ile Pro Gly Asp Val Val Arg Lys Val Leu Lys Ser Asp<br>340 345 350 | | 1056 |
| gtt tcc gca ttg gtt gag ttg aac att gct aag aat ttg gtt gga tct<br>Val Ser Ala Leu Val Glu Leu Asn Ile Ala Lys Asn Leu Val Gly Ser<br>355 360 365 | | 1104 |
| gca atg gct ggg tct gtt ggt gga ttt aac gca cat gca gct aat tta<br>Ala Met Ala Gly Ser Val Gly Gly Phe Asn Ala His Ala Ala Asn Leu<br>370 375 380 | | 1152 |
| gtg aca gct gtt ttc ttg gca tta gga caa gat cct gca caa aat gtt<br>Val Thr Ala Val Phe Leu Ala Leu Gly Gln Asp Pro Ala Gln Asn Val<br>385 390 395 400 | | 1200 |
| gaa agt tcc aac tgt ata aca ttg atg aaa gaa gtg gac ggt gat ttg<br>Glu Ser Ser Asn Cys Ile Thr Leu Met Lys Glu Val Asp Gly Asp Leu<br>405 410 415 | | 1248 |
| aga att tcc gta tcc atg cca tcc atc gaa gta ggt acc atc ggt ggt<br>Arg Ile Ser Val Ser Met Pro Ser Ile Glu Val Gly Thr Ile Gly Gly<br>420 425 430 | | 1296 |
| ggt act gtt cta gaa cca caa ggt gcc atg ttg gac tta tta ggt gta<br>Gly Thr Val Leu Glu Pro Gln Gly Ala Met Leu Asp Leu Leu Gly Val<br>435 440 445 | | 1344 |
| aga ggc ccg cat gct acc gct cct ggt acc aac gca cgt caa tta gca<br>Arg Gly Pro His Ala Thr Ala Pro Gly Thr Asn Ala Arg Gln Leu Ala<br>450 455 460 | | 1392 |
| aga ata gtt gcc tgt gcc gtc ttg gca ggt gaa tta tcc tta tgt gct<br>Arg Ile Val Ala Cys Ala Val Leu Ala Gly Glu Leu Ser Leu Cys Ala<br>465 470 475 480 | | 1440 |
| gcc cta gca gcc ggc cat ttg gtt caa agt cat atg acc cac aac agg<br>Ala Leu Ala Ala Gly His Leu Val Gln Ser His Met Thr His Asn Arg<br>485 490 495 | | 1488 |
| aaa cct gct gaa cca aca aaa cct aac aat ttg gac gcc act gat ata<br>Lys Pro Ala Glu Pro Thr Lys Pro Asn Asn Leu Asp Ala Thr Asp Ile<br>500 505 510 | | 1536 |

-continued

```
aat cgt ttg aaa gat ggg tcc gtc acc tgc att aaa tcc taa         1578
Asn Arg Leu Lys Asp Gly Ser Val Thr Cys Ile Lys Ser
        515                 520                 525
```

<210> SEQ ID NO 4
<211> LENGTH: 525
<212> TYPE: PRT
<213> ORGANISM: Artificial sequence
<220> FEATURE:
<223> OTHER INFORMATION: Description of synthetic sequence: truncated
      HMG-CoA reductase (t-HMG)

<400> SEQUENCE: 4

```
Met Asp Gln Leu Val Lys Thr Glu Val Thr Lys Lys Ser Phe Thr Ala
1               5                   10                  15

Pro Val Gln Lys Ala Ser Thr Pro Val Leu Thr Asn Lys Thr Val Ile
            20                  25                  30

Ser Gly Ser Lys Val Lys Ser Leu Ser Ser Ala Gln Ser Ser Ser Ser
        35                  40                  45

Gly Pro Ser Ser Ser Ser Glu Glu Asp Asp Ser Arg Asp Ile Glu Ser
    50                  55                  60

Leu Asp Lys Lys Ile Arg Pro Leu Glu Glu Leu Glu Ala Leu Leu Ser
65                  70                  75                  80

Ser Gly Asn Thr Lys Gln Leu Lys Asn Lys Glu Val Ala Ala Leu Val
                85                  90                  95

Ile His Gly Lys Leu Pro Leu Tyr Ala Leu Glu Lys Lys Leu Gly Asp
            100                 105                 110

Thr Thr Arg Ala Val Ala Val Arg Arg Lys Ala Leu Ser Ile Leu Ala
        115                 120                 125

Glu Ala Pro Val Leu Ala Ser Asp Arg Leu Pro Tyr Lys Asn Tyr Asp
    130                 135                 140

Tyr Asp Arg Val Phe Gly Ala Cys Cys Glu Asn Val Ile Gly Tyr Met
145                 150                 155                 160

Pro Leu Pro Val Gly Val Ile Gly Pro Leu Val Ile Asp Gly Thr Ser
                165                 170                 175

Tyr His Ile Pro Met Ala Thr Thr Glu Gly Cys Leu Val Ala Ser Ala
            180                 185                 190

Met Arg Gly Cys Lys Ala Ile Asn Ala Gly Gly Gly Ala Thr Thr Val
        195                 200                 205

Leu Thr Lys Asp Gly Met Thr Arg Gly Pro Val Val Arg Phe Pro Thr
    210                 215                 220

Leu Lys Arg Ser Gly Ala Cys Lys Ile Trp Leu Asp Ser Glu Glu Gly
225                 230                 235                 240

Gln Asn Ala Ile Lys Lys Ala Phe Asn Ser Thr Ser Arg Phe Ala Arg
                245                 250                 255

Leu Gln His Ile Gln Thr Cys Leu Ala Gly Asp Leu Leu Phe Met Arg
            260                 265                 270

Phe Arg Thr Thr Thr Gly Asp Ala Met Gly Met Asn Met Ile Ser Lys
        275                 280                 285

Gly Val Glu Tyr Ser Leu Lys Gln Met Val Glu Glu Tyr Gly Trp Glu
    290                 295                 300

Asp Met Glu Val Val Ser Val Ser Gly Asn Tyr Cys Thr Asp Lys Lys
305                 310                 315                 320

Pro Ala Ala Ile Asn Trp Ile Glu Gly Arg Gly Lys Ser Val Val Ala
                325                 330                 335
```

```
Glu Ala Thr Ile Pro Gly Asp Val Val Arg Lys Val Leu Lys Ser Asp
                340                 345                 350

Val Ser Ala Leu Val Glu Leu Asn Ile Ala Lys Asn Leu Val Gly Ser
            355                 360                 365

Ala Met Ala Gly Ser Val Gly Gly Phe Asn Ala His Ala Ala Asn Leu
        370                 375                 380

Val Thr Ala Val Phe Leu Ala Leu Gly Gln Asp Pro Ala Gln Asn Val
385                 390                 395                 400

Glu Ser Ser Asn Cys Ile Thr Leu Met Lys Glu Val Asp Gly Asp Leu
                405                 410                 415

Arg Ile Ser Val Ser Met Pro Ser Ile Glu Val Gly Thr Ile Gly Gly
            420                 425                 430

Gly Thr Val Leu Glu Pro Gln Gly Ala Met Leu Asp Leu Leu Gly Val
        435                 440                 445

Arg Gly Pro His Ala Thr Ala Pro Gly Thr Asn Ala Arg Gln Leu Ala
    450                 455                 460

Arg Ile Val Ala Cys Ala Val Leu Ala Gly Glu Leu Ser Leu Cys Ala
465                 470                 475                 480

Ala Leu Ala Ala Gly His Leu Val Gln Ser His Met Thr His Asn Arg
                485                 490                 495

Lys Pro Ala Glu Pro Thr Lys Pro Asn Asn Leu Asp Ala Thr Asp Ile
            500                 505                 510

Asn Arg Leu Lys Asp Gly Ser Val Thr Cys Ile Lys Ser
        515                 520                 525

<210> SEQ ID NO 5
<211> LENGTH: 1593
<212> TYPE: DNA
<213> ORGANISM: Saccharomyces cerevisiae
<220> FEATURE:
<221> NAME/KEY: CDS
<222> LOCATION: (1)..(1593)

<400> SEQUENCE: 5 atg tct gct acc aag tca atc gtt gga gag gca ttg gaa tac gta aac      48
Met Ser Ala Thr Lys Ser Ile Val Gly Glu Ala Leu Glu Tyr Val Asn
1               5                   10                  15 att ggt tta agt cat ttc ttg gct tta cca ttg gcc caa aga atc tct      96
Ile Gly Leu Ser His Phe Leu Ala Leu Pro Leu Ala Gln Arg Ile Ser
                20                  25                  30 ttg atc ata ata att cct ttc att tac aat att gta tgg caa tta cta     144
Leu Ile Ile Ile Ile Pro Phe Ile Tyr Asn Ile Val Trp Gln Leu Leu
            35                  40                  45 tat tct ttg aga aag gac cgt cca cct cta gtg ttt tac tgg att cca     192
Tyr Ser Leu Arg Lys Asp Arg Pro Pro Leu Val Phe Tyr Trp Ile Pro
        50                  55                  60 tgg gtc ggt agt gct gtt gtg tac ggt atg aag cca tac gag ttt ttc     240
Trp Val Gly Ser Ala Val Val Tyr Gly Met Lys Pro Tyr Glu Phe Phe
65                  70                  75                  80 gaa gaa tgt caa aag aaa tac ggt gat att ttt tca ttc gtt ttg tta     288
Glu Glu Cys Gln Lys Lys Tyr Gly Asp Ile Phe Ser Phe Val Leu Leu
                85                  90                  95 gga aga gtc atg act gtg tat tta gga cca aag ggt cac gaa ttt gtc     336
Gly Arg Val Met Thr Val Tyr Leu Gly Pro Lys Gly His Glu Phe Val
                100                 105                 110 ttc aac gct aag ttg gca gat gtt tca gca gaa gct gct tac gct cat     384
Phe Asn Ala Lys Leu Ala Asp Val Ser Ala Glu Ala Ala Tyr Ala His
            115                 120                 125
```

|   |   |   |   |   |   |   |   |   |   |   |   |   |   |   |   |   |
|---|---|---|---|---|---|---|---|---|---|---|---|---|---|---|---|---|
| ttg | act | act | cca | gtt | ttc | ggt | aaa | ggt | gtt | att | tac | gat | tgt | cca | aat | 432 |
| Leu | Thr | Thr | Pro | Val | Phe | Gly | Lys | Gly | Val | Ile | Tyr | Asp | Cys | Pro | Asn | |
| | 130 | | | | 135 | | | | 140 | | | | | | | |

| tct | aga | ttg | atg | gag | caa | aag | aag | ttt | gtt | aag | ggt | gct | cta | acc | aaa | 480 |
| Ser | Arg | Leu | Met | Glu | Gln | Lys | Lys | Phe | Val | Lys | Gly | Ala | Leu | Thr | Lys | |
| 145 | | | | | 150 | | | | | 155 | | | | | 160 | |

| gaa | gcc | ttc | aag | agc | tac | gtt | cca | ttg | att | gct | gaa | gaa | gtg | tac | aag | 528 |
| Glu | Ala | Phe | Lys | Ser | Tyr | Val | Pro | Leu | Ile | Ala | Glu | Glu | Val | Tyr | Lys | |
| | | | | 165 | | | | | 170 | | | | | 175 | | |

| tac | ttc | aga | gac | tcc | aaa | aac | ttc | cgt | ttg | aat | gaa | aga | act | act | ggt | 576 |
| Tyr | Phe | Arg | Asp | Ser | Lys | Asn | Phe | Arg | Leu | Asn | Glu | Arg | Thr | Thr | Gly | |
| | | | 180 | | | | | 185 | | | | | 190 | | | |

| act | att | gac | gtg | atg | gtt | act | caa | cct | gaa | atg | act | att | ttc | acc | gct | 624 |
| Thr | Ile | Asp | Val | Met | Val | Thr | Gln | Pro | Glu | Met | Thr | Ile | Phe | Thr | Ala | |
| | | 195 | | | | | 200 | | | | | 205 | | | | |

| tca | aga | tca | tta | ttg | ggt | aag | gaa | atg | aga | gca | aaa | ttg | gat | acc | gat | 672 |
| Ser | Arg | Ser | Leu | Leu | Gly | Lys | Glu | Met | Arg | Ala | Lys | Leu | Asp | Thr | Asp | |
| | 210 | | | | | 215 | | | | | 220 | | | | | |

| ttt | gct | tac | ttg | tac | agt | gat | ttg | gat | aag | ggt | ttc | act | cca | atc | aac | 720 |
| Phe | Ala | Tyr | Leu | Tyr | Ser | Asp | Leu | Asp | Lys | Gly | Phe | Thr | Pro | Ile | Asn | |
| 225 | | | | | 230 | | | | | 235 | | | | | 240 | |

| ttc | gtc | ttc | cct | aac | tta | cca | ttg | gaa | cac | tat | aga | aag | aga | gat | cac | 768 |
| Phe | Val | Phe | Pro | Asn | Leu | Pro | Leu | Glu | His | Tyr | Arg | Lys | Arg | Asp | His | |
| | | | | 245 | | | | | 250 | | | | | 255 | | |

| gct | caa | aag | gct | atc | tcc | ggt | act | tac | atg | tct | ttg | att | aag | gaa | aga | 816 |
| Ala | Gln | Lys | Ala | Ile | Ser | Gly | Thr | Tyr | Met | Ser | Leu | Ile | Lys | Glu | Arg | |
| | | | 260 | | | | | 265 | | | | | 270 | | | |

| aga | aag | aac | aac | gac | att | caa | gac | aga | gat | ttg | atc | gat | tcc | ttg | atg | 864 |
| Arg | Lys | Asn | Asn | Asp | Ile | Gln | Asp | Arg | Asp | Leu | Ile | Asp | Ser | Leu | Met | |
| | | 275 | | | | | 280 | | | | | 285 | | | | |

| aag | aac | tct | acc | tac | aag | gat | ggt | gtg | aag | atg | act | gat | caa | gaa | atc | 912 |
| Lys | Asn | Ser | Thr | Tyr | Lys | Asp | Gly | Val | Lys | Met | Thr | Asp | Gln | Glu | Ile | |
| | 290 | | | | | 295 | | | | | 300 | | | | | |

| gct | aac | ttg | tta | att | ggt | gtc | tta | atg | ggt | ggt | caa | cat | act | tct | gct | 960 |
| Ala | Asn | Leu | Leu | Ile | Gly | Val | Leu | Met | Gly | Gly | Gln | His | Thr | Ser | Ala | |
| 305 | | | | | 310 | | | | | 315 | | | | | 320 | |

| gcc | act | tct | gct | tgg | att | ttg | ttg | cac | ttg | gct | gaa | aga | cca | gat | gtc | 1008 |
| Ala | Thr | Ser | Ala | Trp | Ile | Leu | Leu | His | Leu | Ala | Glu | Arg | Pro | Asp | Val | |
| | | | | 325 | | | | | 330 | | | | | 335 | | |

| caa | caa | gaa | ttg | tac | gaa | gaa | caa | atg | cgt | gtt | ttg | gat | ggt | ggt | aag | 1056 |
| Gln | Gln | Glu | Leu | Tyr | Glu | Glu | Gln | Met | Arg | Val | Leu | Asp | Gly | Gly | Lys | |
| | | | 340 | | | | | 345 | | | | | 350 | | | |

| aag | gaa | ttg | acc | tac | gat | tta | tta | caa | gaa | atg | cca | ttg | ttg | aac | caa | 1104 |
| Lys | Glu | Leu | Thr | Tyr | Asp | Leu | Leu | Gln | Glu | Met | Pro | Leu | Leu | Asn | Gln | |
| | | 355 | | | | | 360 | | | | | 365 | | | | |

| act | att | aag | gaa | act | cta | aga | atg | cac | cat | cca | ttg | cac | tct | ttg | ttc | 1152 |
| Thr | Ile | Lys | Glu | Thr | Leu | Arg | Met | His | His | Pro | Leu | His | Ser | Leu | Phe | |
| | 370 | | | | | 375 | | | | | 380 | | | | | |

| cgt | aag | gtt | atg | aaa | gat | atg | cac | gtt | cca | aac | act | tct | tat | gtc | atc | 1200 |
| Arg | Lys | Val | Met | Lys | Asp | Met | His | Val | Pro | Asn | Thr | Ser | Tyr | Val | Ile | |
| 385 | | | | | 390 | | | | | 395 | | | | | 400 | |

| cca | gca | ggt | tat | cac | gtt | ttg | gtt | tct | cca | ggt | tac | act | cat | tta | aga | 1248 |
| Pro | Ala | Gly | Tyr | His | Val | Leu | Val | Ser | Pro | Gly | Tyr | Thr | His | Leu | Arg | |
| | | | | 405 | | | | | 410 | | | | | 415 | | |

| gac | gaa | tac | ttc | cct | aat | gct | cac | caa | ttc | aac | att | cac | cgt | tgg | aac | 1296 |
| Asp | Glu | Tyr | Phe | Pro | Asn | Ala | His | Gln | Phe | Asn | Ile | His | Arg | Trp | Asn | |
| | | | 420 | | | | | 425 | | | | | 430 | | | |

| aaa | gat | tct | gcc | tcc | tct | tat | tcc | gtc | ggt | gaa | gaa | gtc | gat | tac | ggt | 1344 |
| Lys | Asp | Ser | Ala | Ser | Ser | Tyr | Ser | Val | Gly | Glu | Glu | Val | Asp | Tyr | Gly | |
| | | 435 | | | | | 440 | | | | | 445 | | | | |

-continued

| | | | |
|---|---|---|---|
| ttc ggt gcc att tct aag ggt gtc agc tct cca tac tta cct ttc ggt<br>Phe Gly Ala Ile Ser Lys Gly Val Ser Ser Pro Tyr Leu Pro Phe Gly<br>450                            455                     460 | 1392 |
| ggt gga aga cac aga tgt atc ggt gaa cac ttt gct tac tgt cag cta<br>Gly Gly Arg His Arg Cys Ile Gly Glu His Phe Ala Tyr Cys Gln Leu<br>465                           470                     475                  480 | 1440 |
| ggt gtt cta atg tcc att ttt atc aga aca tta aaa tgg cat tac cca<br>Gly Val Leu Met Ser Ile Phe Ile Arg Thr Leu Lys Trp His Tyr Pro<br>                      485                     490                     495 | 1488 |
| gag ggt aag acc gtt cca cct cct gac ttt aca tct atg gtt act ctt<br>Glu Gly Lys Thr Val Pro Pro Pro Asp Phe Thr Ser Met Val Thr Leu<br>500                           505                     510 | 1536 |
| cca acc ggt cca gcc aag atc atc tgg gaa aag aga aat cca gaa caa<br>Pro Thr Gly Pro Ala Lys Ile Ile Trp Glu Lys Arg Asn Pro Glu Gln<br>               515                     520                     525 | 1584 |
| aag atc taa<br>Lys Ile<br>      530 | 1593 |

<210> SEQ ID NO 6
<211> LENGTH: 530
<212> TYPE: PRT
<213> ORGANISM: Saccharomyces cerevisiae

<400> SEQUENCE: 6

Met Ser Ala Thr Lys Ser Ile Val Gly Glu Ala Leu Glu Tyr Val Asn
1                 5                    10               15

Ile Gly Leu Ser His Phe Leu Ala Leu Pro Leu Ala Gln Arg Ile Ser
               20                    25                    30

Leu Ile Ile Ile Ile Pro Phe Ile Tyr Asn Ile Val Trp Gln Leu Leu
           35                    40                    45

Tyr Ser Leu Arg Lys Asp Arg Pro Pro Leu Val Phe Tyr Trp Ile Pro
50                    55                    60

Trp Val Gly Ser Ala Val Val Tyr Gly Met Lys Pro Tyr Glu Phe Phe
65                70                    75                    80

Glu Glu Cys Gln Lys Lys Tyr Gly Asp Ile Phe Ser Phe Val Leu Leu
                   85                    90                    95

Gly Arg Val Met Thr Val Tyr Leu Gly Pro Lys Gly His Glu Phe Val
                  100                 105               110

Phe Asn Ala Lys Leu Ala Asp Val Ser Ala Glu Ala Ala Tyr Ala His
           115                  120                 125

Leu Thr Thr Pro Val Phe Gly Lys Gly Val Ile Tyr Asp Cys Pro Asn
130                   135                 140

Ser Arg Leu Met Glu Gln Lys Lys Phe Val Lys Gly Ala Leu Thr Lys
145               150                    155               160

Glu Ala Phe Lys Ser Tyr Val Pro Leu Ile Ala Glu Glu Val Tyr Lys
                 165                 170               175

Tyr Phe Arg Asp Ser Lys Asn Phe Arg Leu Asn Glu Arg Thr Thr Gly
           180                  185                 190

Thr Ile Asp Val Met Val Thr Gln Pro Glu Met Thr Ile Phe Thr Ala
195                   200                 205

Ser Arg Ser Leu Leu Gly Lys Glu Met Arg Ala Lys Leu Asp Thr Asp
210               215                    220

Phe Ala Tyr Leu Tyr Ser Asp Leu Asp Lys Gly Phe Thr Pro Ile Asn
225               230                    235               240

Phe Val Phe Pro Asn Leu Pro Leu Glu His Tyr Arg Lys Arg Asp His

-continued

```
                        245                 250                 255
Ala Gln Lys Ala Ile Ser Gly Thr Tyr Met Ser Leu Ile Lys Glu Arg
            260                 265                 270

Arg Lys Asn Asn Asp Ile Gln Asp Arg Asp Leu Ile Asp Ser Leu Met
        275                 280                 285

Lys Asn Ser Thr Tyr Lys Asp Gly Val Lys Met Thr Asp Gln Glu Ile
    290                 295                 300

Ala Asn Leu Leu Ile Gly Val Leu Met Gly Gly Gln His Thr Ser Ala
305                 310                 315                 320

Ala Thr Ser Ala Trp Ile Leu Leu His Leu Ala Glu Arg Pro Asp Val
                325                 330                 335

Gln Gln Glu Leu Tyr Glu Glu Gln Met Arg Val Leu Asp Gly Gly Lys
            340                 345                 350

Lys Glu Leu Thr Tyr Asp Leu Leu Gln Glu Met Pro Leu Leu Asn Gln
        355                 360                 365

Thr Ile Lys Glu Thr Leu Arg Met His His Pro Leu His Ser Leu Phe
    370                 375                 380

Arg Lys Val Met Lys Asp Met His Val Pro Asn Thr Ser Tyr Val Ile
385                 390                 395                 400

Pro Ala Gly Tyr His Val Leu Val Ser Pro Gly Tyr Thr His Leu Arg
                405                 410                 415

Asp Glu Tyr Phe Pro Asn Ala His Gln Phe Asn Ile His Arg Trp Asn
            420                 425                 430

Lys Asp Ser Ala Ser Ser Tyr Ser Val Gly Glu Glu Val Asp Tyr Gly
        435                 440                 445

Phe Gly Ala Ile Ser Lys Gly Val Ser Ser Pro Tyr Leu Pro Phe Gly
    450                 455                 460

Gly Gly Arg His Arg Cys Ile Gly Glu His Phe Ala Tyr Cys Gln Leu
465                 470                 475                 480

Gly Val Leu Met Ser Ile Phe Ile Arg Thr Leu Lys Trp His Tyr Pro
                485                 490                 495

Glu Gly Lys Thr Val Pro Pro Asp Phe Thr Ser Met Val Thr Leu
            500                 505                 510

Pro Thr Gly Pro Ala Lys Ile Ile Trp Glu Lys Arg Asn Pro Glu Gln
        515                 520                 525

Lys Ile
    530

<210> SEQ ID NO 7
<211> LENGTH: 1491
<212> TYPE: DNA
<213> ORGANISM: Saccharomyces cerevisiae
<220> FEATURE:
<221> NAME/KEY: CDS
<222> LOCATION: (1)..(1491)

<400> SEQUENCE: 7 atg tct gct gtt aac gtt gca cct gaa ttg att aat gcc gac aac aca       48
Met Ser Ala Val Asn Val Ala Pro Glu Leu Ile Asn Ala Asp Asn Thr
1               5                   10                  15 att acc tac gat gcg att gtc atc ggt gct ggt gtt atc ggt cca tgt       96
Ile Thr Tyr Asp Ala Ile Val Ile Gly Ala Gly Val Ile Gly Pro Cys
            20                  25                  30 gtt gct act ggt cta gca aga aag ggt aag aaa gtt ctt atc gta gaa      144
Val Ala Thr Gly Leu Ala Arg Lys Gly Lys Lys Val Leu Ile Val Glu
        35                  40                  45
```

-continued

| | | |
|---|---|---|
| cgt gac tgg gct atg cct gat aga att gtt ggt gaa ttg atg caa cca<br>Arg Asp Trp Ala Met Pro Asp Arg Ile Val Gly Glu Leu Met Gln Pro<br>50              55                  60 | | 192 |
| ggt ggt gtt aga gca ttg aga agt ctg ggt atg att caa tct atc aac<br>Gly Gly Val Arg Ala Leu Arg Ser Leu Gly Met Ile Gln Ser Ile Asn<br>65              70                  75              80 | | 240 |
| aac atc gaa gca tat cct gtt acc ggt tat acc gtc ttt ttc aac ggc<br>Asn Ile Glu Ala Tyr Pro Val Thr Gly Tyr Thr Val Phe Phe Asn Gly<br>        85                  90                  95 | | 288 |
| gaa caa gtt gat att cca tac cct tac aag gcc gat atc cct aaa gtt<br>Glu Gln Val Asp Ile Pro Tyr Pro Tyr Lys Ala Asp Ile Pro Lys Val<br>            100                 105                 110 | | 336 |
| gaa aaa ttg aag gac ttg gtc aaa gat ggt aat gac aag gtc ttg gaa<br>Glu Lys Leu Lys Asp Leu Val Lys Asp Gly Asn Asp Lys Val Leu Glu<br>        115                 120                 125 | | 384 |
| gac agc act att cac atc aag gat tac gaa gat gat gaa aga gaa agg<br>Asp Ser Thr Ile His Ile Lys Asp Tyr Glu Asp Asp Glu Arg Glu Arg<br>130                 135                 140 | | 432 |
| ggt gtt gct ttt gtt cat ggt aga ttc ttg aac aac ttg aga aac att<br>Gly Val Ala Phe Val His Gly Arg Phe Leu Asn Asn Leu Arg Asn Ile<br>145                 150                 155                 160 | | 480 |
| act gct caa gag cca aat gtt act aga gtg caa ggt aac tgt att gag<br>Thr Ala Gln Glu Pro Asn Val Thr Arg Val Gln Gly Asn Cys Ile Glu<br>            165                 170                 175 | | 528 |
| ata ttg aag gat gaa aag aat gag gtt gtt ggt gcc aag gtt gac att<br>Ile Leu Lys Asp Glu Lys Asn Glu Val Val Gly Ala Lys Val Asp Ile<br>        180                 185                 190 | | 576 |
| gat ggc cgt ggc aag gtg gaa ttc aaa gcc cac ttg aca ttt atc tgt<br>Asp Gly Arg Gly Lys Val Glu Phe Lys Ala His Leu Thr Phe Ile Cys<br>            195                 200                 205 | | 624 |
| gac ggt atc ttt tca cgt ttc aga aag gaa ttg cac cca gac cat gtt<br>Asp Gly Ile Phe Ser Arg Phe Arg Lys Glu Leu His Pro Asp His Val<br>210                 215                 220 | | 672 |
| cca act gtc ggt tct tcg ttt gtc ggt atg tct ttg ttc aat gct aag<br>Pro Thr Val Gly Ser Ser Phe Val Gly Met Ser Leu Phe Asn Ala Lys<br>225                 230                 235                 240 | | 720 |
| aat cct gct cct atg cac ggt cac gtt att ctt ggt agt gat cat atg<br>Asn Pro Ala Pro Met His Gly His Val Ile Leu Gly Ser Asp His Met<br>            245                 250                 255 | | 768 |
| cca atc ttg gtt tac caa atc agt cca gaa gaa aca aga atc ctt tgt<br>Pro Ile Leu Val Tyr Gln Ile Ser Pro Glu Glu Thr Arg Ile Leu Cys<br>        260                 265                 270 | | 816 |
| gct tac aac tct cca aag gtc cca gct gat atc aag agt tgg atg att<br>Ala Tyr Asn Ser Pro Lys Val Pro Ala Asp Ile Lys Ser Trp Met Ile<br>            275                 280                 285 | | 864 |
| aag gat gtc caa cct ttc att cca aag agt cta cgt cct tca ttt gat<br>Lys Asp Val Gln Pro Phe Ile Pro Lys Ser Leu Arg Pro Ser Phe Asp<br>290                 295                 300 | | 912 |
| gaa gcc gtc agc caa ggt aaa ttt aga gct atg cca aac tcc tac ttg<br>Glu Ala Val Ser Gln Gly Lys Phe Arg Ala Met Pro Asn Ser Tyr Leu<br>305                 310                 315                 320 | | 960 |
| cca gct aga caa aac gac gtc act ggt atg tgt gtt atc ggt gac gct<br>Pro Ala Arg Gln Asn Asp Val Thr Gly Met Cys Val Ile Gly Asp Ala<br>            325                 330                 335 | | 1008 |
| cta aat atg aga cat cca ttg act ggt ggt ggt atg act gtc ggt ttg<br>Leu Asn Met Arg His Pro Leu Thr Gly Gly Gly Met Thr Val Gly Leu<br>        340                 345                 350 | | 1056 |
| cat gat gtt gtc ttg ttg att aag aaa ata ggt gac cta gac ttc agc<br>His Asp Val Val Leu Leu Ile Lys Lys Ile Gly Asp Leu Asp Phe Ser<br>            355                 360                 365 | | 1104 |

```
gac cgt gaa aag gtt ttg gat gaa tta cta gac tac cat ttc gaa aga     1152
Asp Arg Glu Lys Val Leu Asp Glu Leu Leu Asp Tyr His Phe Glu Arg
    370                 375                 380 aag agt tac gat tcc gtt att aac gtt ttg tca gtg gct ttg tat tct     1200
Lys Ser Tyr Asp Ser Val Ile Asn Val Leu Ser Val Ala Leu Tyr Ser
385                 390                 395                 400 ttg ttc gct gct gac agc gat aac ttg aag gca tta caa aaa ggt tgt     1248
Leu Phe Ala Ala Asp Ser Asp Asn Leu Lys Ala Leu Gln Lys Gly Cys
                405                 410                 415 ttc aaa tat ttc caa aga ggt ggc gat tgt gtc aac aaa ccc gtt gaa     1296
Phe Lys Tyr Phe Gln Arg Gly Gly Asp Cys Val Asn Lys Pro Val Glu
            420                 425                 430 ttt ctg tct ggt gtc ttg cca aag cct ttg caa ttg acc agg gtt ttc     1344
Phe Leu Ser Gly Val Leu Pro Lys Pro Leu Gln Leu Thr Arg Val Phe
        435                 440                 445 ttc gct gtc gct ttt tac acc att tac ttg aac atg gaa gaa cgt ggt     1392
Phe Ala Val Ala Phe Tyr Thr Ile Tyr Leu Asn Met Glu Glu Arg Gly
    450                 455                 460 ttc ttg gga tta cca atg gct tta ttg gaa ggt att atg att ttg atc     1440
Phe Leu Gly Leu Pro Met Ala Leu Leu Glu Gly Ile Met Ile Leu Ile
465                 470                 475                 480 aca gct att aga gta ttc acc cca ttt ttg ttt ggt gag ttg att ggt     1488
Thr Ala Ile Arg Val Phe Thr Pro Phe Leu Phe Gly Glu Leu Ile Gly
                485                 490                 495 taa                                                                  1491

<210> SEQ ID NO 8
<211> LENGTH: 496
<212> TYPE: PRT
<213> ORGANISM: Saccharomyces cerevisiae

<400> SEQUENCE: 8

Met Ser Ala Val Asn Val Ala Pro Glu Leu Ile Asn Ala Asp Asn Thr
1               5                   10                  15

Ile Thr Tyr Asp Ala Ile Val Ile Gly Ala Gly Val Ile Gly Pro Cys
            20                  25                  30

Val Ala Thr Gly Leu Ala Arg Lys Gly Lys Lys Val Leu Ile Val Glu
        35                  40                  45

Arg Asp Trp Ala Met Pro Asp Arg Ile Val Gly Glu Leu Met Gln Pro
    50                  55                  60

Gly Gly Val Arg Ala Leu Arg Ser Leu Gly Met Ile Gln Ser Ile Asn
65                  70                  75                  80

Asn Ile Glu Ala Tyr Pro Val Thr Gly Tyr Thr Val Phe Phe Asn Gly
                85                  90                  95

Glu Gln Val Asp Ile Pro Tyr Pro Tyr Lys Ala Asp Ile Pro Lys Val
            100                 105                 110

Glu Lys Leu Lys Asp Leu Val Lys Asp Gly Asn Asp Lys Val Leu Glu
        115                 120                 125

Asp Ser Thr Ile His Ile Lys Asp Tyr Glu Asp Glu Arg Glu Arg
    130                 135                 140

Gly Val Ala Phe Val His Gly Arg Phe Leu Asn Asn Leu Arg Asn Ile
145                 150                 155                 160

Thr Ala Gln Glu Pro Asn Val Thr Arg Val Gln Gly Asn Cys Ile Glu
                165                 170                 175

Ile Leu Lys Asp Glu Lys Asn Glu Val Val Gly Ala Lys Val Asp Ile
            180                 185                 190
```

```
Asp Gly Arg Gly Lys Val Glu Phe Lys Ala His Leu Thr Phe Ile Cys
        195                 200                 205

Asp Gly Ile Phe Ser Arg Phe Arg Lys Glu Leu His Pro Asp His Val
        210                 215                 220

Pro Thr Val Gly Ser Ser Phe Val Gly Met Ser Leu Phe Asn Ala Lys
225                 230                 235                 240

Asn Pro Ala Pro Met His Gly His Val Ile Leu Gly Ser Asp His Met
                245                 250                 255

Pro Ile Leu Val Tyr Gln Ile Ser Pro Glu Thr Arg Ile Leu Cys
        260                 265                 270

Ala Tyr Asn Ser Pro Lys Val Pro Ala Asp Ile Lys Ser Trp Met Ile
        275                 280                 285

Lys Asp Val Gln Pro Phe Ile Pro Lys Ser Leu Arg Pro Ser Phe Asp
        290                 295                 300

Glu Ala Val Ser Gln Gly Lys Phe Arg Ala Met Pro Asn Ser Tyr Leu
305                 310                 315                 320

Pro Ala Arg Gln Asn Asp Val Thr Gly Met Cys Val Ile Gly Asp Ala
                325                 330                 335

Leu Asn Met Arg His Pro Leu Thr Gly Gly Met Thr Val Gly Leu
        340                 345                 350

His Asp Val Val Leu Leu Ile Lys Lys Ile Gly Asp Leu Asp Phe Ser
        355                 360                 365

Asp Arg Glu Lys Val Leu Asp Glu Leu Leu Asp Tyr His Phe Glu Arg
        370                 375                 380

Lys Ser Tyr Asp Ser Val Ile Asn Val Leu Ser Val Ala Leu Tyr Ser
385                 390                 395                 400

Leu Phe Ala Ala Asp Ser Asp Asn Leu Lys Ala Leu Gln Lys Gly Cys
                405                 410                 415

Phe Lys Tyr Phe Gln Arg Gly Gly Asp Cys Val Asn Lys Pro Val Glu
                420                 425                 430

Phe Leu Ser Gly Val Leu Pro Lys Pro Leu Gln Leu Thr Arg Val Phe
        435                 440                 445

Phe Ala Val Ala Phe Tyr Thr Ile Tyr Leu Asn Met Glu Glu Arg Gly
        450                 455                 460

Phe Leu Gly Leu Pro Met Ala Leu Leu Glu Gly Ile Met Ile Leu Ile
465                 470                 475                 480

Thr Ala Ile Arg Val Phe Thr Pro Phe Leu Phe Gly Glu Leu Ile Gly
                485                 490                 495

<210> SEQ ID NO 9
<211> LENGTH: 1335
<212> TYPE: DNA
<213> ORGANISM: Saccharomyces cerevisiae
<220> FEATURE:
<221> NAME/KEY: CDS
<222> LOCATION: (1)..(1335)

<400> SEQUENCE: 9 atg gga aag cta tta caa ttg gca ttg cat ccg gtc gag atg aag gca    48
Met Gly Lys Leu Leu Gln Leu Ala Leu His Pro Val Glu Met Lys Ala
1               5                   10                  15 gct ttg aag ctg aag ttt tgc aga aca ccg cta ttc tcc atc tat gat    96
Ala Leu Lys Leu Lys Phe Cys Arg Thr Pro Leu Phe Ser Ile Tyr Asp
                20                  25                  30 cag tcc acg tct cca tat ctc ttg cac tgt ttc gaa ctg ttg aac ttg   144
Gln Ser Thr Ser Pro Tyr Leu Leu His Cys Phe Glu Leu Leu Asn Leu
        35                  40                  45
```

-continued

| | | |
|---|---|---|
| acc tcc aga tcg ttt gct gct gtg atc aga gag ctg cat cca gaa ttg<br>Thr Ser Arg Ser Phe Ala Ala Val Ile Arg Glu Leu His Pro Glu Leu<br>50                              55                       60 | 192 |
| aga aac tgt gtt act ctc ttt tat ttg att tta agg gct ttg gat acc<br>Arg Asn Cys Val Thr Leu Phe Tyr Leu Ile Leu Arg Ala Leu Asp Thr<br>65                      70                   75                         80 | 240 |
| atc gaa gac gat atg tcc atc gaa cac gat ttg aaa att gac ttg ttg<br>Ile Glu Asp Asp Met Ser Ile Glu His Asp Leu Lys Ile Asp Leu Leu<br>                       85                       90                        95 | 288 |
| cgt cac ttc cac gag aaa ttg ttg tta act aaa tgg agt ttc gac gga<br>Arg His Phe His Glu Lys Leu Leu Leu Thr Lys Trp Ser Phe Asp Gly<br>                100                    105                   110 | 336 |
| aat gcc ccc gat gtg aag gac aga gcc gtt ttg aca gat ttc gaa tcg<br>Asn Ala Pro Asp Val Lys Asp Arg Ala Val Leu Thr Asp Phe Glu Ser<br>              115                    120                   125 | 384 |
| att ctt att gaa ttc cac aaa ttg aaa cca gaa tat caa gaa gtc atc<br>Ile Leu Ile Glu Phe His Lys Leu Lys Pro Glu Tyr Gln Glu Val Ile<br>130                      135                    140 | 432 |
| aag gag atc acc gag aaa atg ggt aat ggt atg gcc gac tac atc tta<br>Lys Glu Ile Thr Glu Lys Met Gly Asn Gly Met Ala Asp Tyr Ile Leu<br>145                      150                    155                   160 | 480 |
| gat gaa aat tac aac ttg aat ggg ttg caa acc gtc cac gac tac gac<br>Asp Glu Asn Tyr Asn Leu Asn Gly Leu Gln Thr Val His Asp Tyr Asp<br>                      165                    170                   175 | 528 |
| gtg tac tgt cac tac gta gct ggt ttg gtc ggt gat ggt ttg acc cgt<br>Val Tyr Cys His Tyr Val Ala Gly Leu Val Gly Asp Gly Leu Thr Arg<br>              180                    185                   190 | 576 |
| ttg att gtc att gcc aag ttt gcc aac gaa tct ttg tat tct aat gag<br>Leu Ile Val Ile Ala Lys Phe Ala Asn Glu Ser Leu Tyr Ser Asn Glu<br>195                      200                    205 | 624 |
| caa ttg tat gaa agc atg ggt ctt ttc cta caa aaa acc aac atc atc<br>Gln Leu Tyr Glu Ser Met Gly Leu Phe Leu Gln Lys Thr Asn Ile Ile<br>210                      215                    220 | 672 |
| aga gat tac aat gaa gat ttg gtc gat ggt aga tcc ttc tgg ccc aag<br>Arg Asp Tyr Asn Glu Asp Leu Val Asp Gly Arg Ser Phe Trp Pro Lys<br>225                      230                    235                   240 | 720 |
| gaa atc tgg tca caa tac gct cct cag ttg aag gac ttc atg aaa cct<br>Glu Ile Trp Ser Gln Tyr Ala Pro Gln Leu Lys Asp Phe Met Lys Pro<br>                      245                    250                   255 | 768 |
| gaa aac gaa caa ctg ggg ttg gac tgt ata aac cac ctc gtc tta aac<br>Glu Asn Glu Gln Leu Gly Leu Asp Cys Ile Asn His Leu Val Leu Asn<br>              260                    265                   270 | 816 |
| gca ttg agt cat gtt atc gat gtg ttg act tat ttg gcc ggt atc cac<br>Ala Leu Ser His Val Ile Asp Val Leu Thr Tyr Leu Ala Gly Ile His<br>275                      280                    285 | 864 |
| gag caa tcc act ttc caa ttt tgt gcc att ccc caa gtt atg gcc att<br>Glu Gln Ser Thr Phe Gln Phe Cys Ala Ile Pro Gln Val Met Ala Ile<br>290                      295                    300 | 912 |
| gca acc ttg gct ttg gta ttc aac aac cgt gaa gtg cta cat ggc aat<br>Ala Thr Leu Ala Leu Val Phe Asn Asn Arg Glu Val Leu His Gly Asn<br>305                      310                    315                   320 | 960 |
| gta aag att cgt aag ggt act acc tgc tat tta att ttg aaa tca agg<br>Val Lys Ile Arg Lys Gly Thr Thr Cys Tyr Leu Ile Leu Lys Ser Arg<br>                      325                    330                   335 | 1008 |
| act ttg cgt ggc tgt gtc gag att ttt gac tat tac tta cgt gat atc<br>Thr Leu Arg Gly Cys Val Glu Ile Phe Asp Tyr Tyr Leu Arg Asp Ile<br>              340                    345                   350 | 1056 |
| aaa tct aaa ttg gct gtg caa gat cca aat ttc tta aaa ttg aac att<br>Lys Ser Lys Leu Ala Val Gln Asp Pro Asn Phe Leu Lys Leu Asn Ile | 1104 |

-continued

```
                     355                 360                 365
caa atc tcc aag atc gaa cag ttt atg gaa gaa atg tac cag gat aaa     1152
Gln Ile Ser Lys Ile Glu Gln Phe Met Glu Glu Met Tyr Gln Asp Lys
        370                 375                 380 tta cct cct aac gtg aag cca aat gaa act cca att ttc ttg aaa gtt     1200
Leu Pro Pro Asn Val Lys Pro Asn Glu Thr Pro Ile Phe Leu Lys Val
385                 390                 395                 400 aaa gaa aga tcc aga tac gat gat gaa ttg gtt cca acc caa caa gaa     1248
Lys Glu Arg Ser Arg Tyr Asp Asp Glu Leu Val Pro Thr Gln Gln Glu
                405                 410                 415 gaa gag tac aag ttc aat atg gtt tta tct atc atc ttg tcc gtt ctt     1296
Glu Glu Tyr Lys Phe Asn Met Val Leu Ser Ile Ile Leu Ser Val Leu
            420                 425                 430 ctt ggg ttt tat tat ata tac act tta cac aga gcg tga                 1335
Leu Gly Phe Tyr Tyr Ile Tyr Thr Leu His Arg Ala
        435                 440
```

<210> SEQ ID NO 10
<211> LENGTH: 444
<212> TYPE: PRT
<213> ORGANISM: Saccharomyces cerevisiae

<400> SEQUENCE: 10

```
Met Gly Lys Leu Leu Gln Leu Ala Leu His Pro Val Glu Met Lys Ala
1               5                   10                  15

Ala Leu Lys Leu Lys Phe Cys Arg Thr Pro Leu Phe Ser Ile Tyr Asp
                20                  25                  30

Gln Ser Thr Ser Pro Tyr Leu Leu His Cys Phe Glu Leu Leu Asn Leu
            35                  40                  45

Thr Ser Arg Ser Phe Ala Ala Val Ile Arg Glu Leu His Pro Glu Leu
        50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
                100                 105                 110

Asn Ala Pro Asp Val Lys Asp Arg Ala Val Leu Thr Asp Phe Glu Ser
            115                 120                 125

Ile Leu Ile Glu Phe His Lys Leu Lys Pro Glu Tyr Gln Glu Val Ile
        130                 135                 140

Lys Glu Ile Thr Glu Lys Met Gly Asn Gly Met Ala Asp Tyr Ile Leu
145                 150                 155                 160

Asp Glu Asn Tyr Asn Leu Asn Gly Leu Gln Thr Val His Asp Tyr Asp
                165                 170                 175

Val Tyr Cys His Tyr Val Ala Gly Leu Val Gly Asp Gly Leu Thr Arg
            180                 185                 190

Leu Ile Val Ile Ala Lys Phe Ala Asn Glu Ser Leu Tyr Ser Asn Glu
        195                 200                 205

Gln Leu Tyr Glu Ser Met Gly Leu Phe Leu Gln Lys Thr Asn Ile Ile
    210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
                245                 250                 255

Glu Asn Glu Gln Leu Gly Leu Asp Cys Ile Asn His Leu Val Leu Asn
```

```
                260              265              270
Ala Leu Ser His Val Ile Asp Val Leu Thr Tyr Leu Ala Gly Ile His
        275              280              285
Glu Gln Ser Thr Phe Gln Phe Cys Ala Ile Pro Gln Val Met Ala Ile
        290              295              300
Ala Thr Leu Ala Leu Val Phe Asn Asn Arg Glu Val Leu His Gly Asn
305              310              315              320
Val Lys Ile Arg Lys Gly Thr Thr Cys Tyr Leu Ile Leu Lys Ser Arg
                325              330              335
Thr Leu Arg Gly Cys Val Glu Ile Phe Asp Tyr Tyr Leu Arg Asp Ile
        340              345              350
Lys Ser Lys Leu Ala Val Gln Asp Pro Asn Phe Leu Lys Leu Asn Ile
        355              360              365
Gln Ile Ser Lys Ile Glu Gln Phe Met Glu Met Tyr Gln Asp Lys
        370              375              380
Leu Pro Pro Asn Val Lys Pro Asn Glu Thr Pro Ile Phe Leu Lys Val
385              390              395              400
Lys Glu Arg Ser Arg Tyr Asp Asp Glu Leu Val Pro Thr Gln Gln Glu
                405              410              415
Glu Glu Tyr Lys Phe Asn Met Val Leu Ser Ile Ile Leu Ser Val Leu
                420              425              430
Leu Gly Phe Tyr Tyr Ile Tyr Thr Leu His Arg Ala
        435              440

<210> SEQ ID NO 11
<211> LENGTH: 35
<212> TYPE: DNA
<213> ORGANISM: Artificial sequence
<220> FEATURE:
<223> OTHER INFORMATION: Description of synthetic sequence: AtHT-5'
<220> FEATURE:
<221> NAME/KEY: misc_feature
<222> LOCATION: (1)..(35)
<223> OTHER INFORMATION: Primer

<400> SEQUENCE: 11
ctgcggccgc atcatggacc aattggtgaa aactg                          35

<210> SEQ ID NO 12
<211> LENGTH: 32
<212> TYPE: DNA
<213> ORGANISM: Artificial sequence
<220> FEATURE:
<223> OTHER INFORMATION: Description of synthetic sequence: AtHT-3'
<220> FEATURE:
<221> NAME/KEY: misc_feature
<222> LOCATION: (1)..(32)
<223> OTHER INFORMATION: Primer

<400> SEQUENCE: 12
aactcgagag acacatggtg ctgttgtgct tc                             32

<210> SEQ ID NO 13
<211> LENGTH: 60
<212> TYPE: DNA
<213> ORGANISM: Artificial sequence
<220> FEATURE:
<223> OTHER INFORMATION: Description of synthetic sequence:
      ERG5-Crelox-5'
<220> FEATURE:
<221> NAME/KEY: misc_feature
<222> LOCATION: (1)..(60)
<223> OTHER INFORMATION: Primer
```

```
<400> SEQUENCE: 13
atgagttctg tcgcagaaaa tataatacaa catgccactc ccagctgaag cttcgtacgc    60

<210> SEQ ID NO 14
<211> LENGTH: 62
<212> TYPE: DNA
<213> ORGANISM: Artificial sequence
<220> FEATURE:
<223> OTHER INFORMATION: Description of synthetic sequence:
      ERG5-Crelox-3'
<220> FEATURE:
<221> NAME/KEY: misc_feature
<222> LOCATION: (1)..(62)
<223> OTHER INFORMATION: Primer

<400> SEQUENCE: 14
ttattcgaag acttctccag taattgggtc tctcttttttg gcataggcca ctagtggatc   60
tg                                                                   62
```

METHOD FOR PRODUCING ERGOSTA-5,7-DIENOL AND/OR BIOSYNTHETIC INTERMEDIATE AND/OR SECONDARY PRODUCTS THEREOF IN TRANSGENIC ORGANISMS

RELATED APPLICATIONS

This application is a national stage application (under 35 U.S.C. 371) of PCT/EP2004/002582 filed Mar. 12, 2004 which claims benefit to German application 103 12 314.8 filed Mar. 19, 2003.

The present invention relates to a method for the production of ergosta-5,7-dienol and/or its biosynthetic intermediates and/or metabolites by culturing genetically modified organisms, and to the genetically modified organisms, in particular yeasts, themselves.

Ergosta-5,7-dienol and its biosynthetic intermediates of the sterol metabolism, such as, for example, farnesol, geraniol, squalene and lanosterol and zymosterol, and its biosynthetic metabolites of the sterol metabolism, for example in mammals, such as, for example, campesterol, pregnenolone, 17-OH-pregnenolone, progesterone, 17-OH-progesterone, 11-deoxycortisol, hydrocortisone, deoxycorticosterone or corticosterone, are compounds of high economical value.

Ergosta-5,7-dienol may act as starting compound for the preparation of steroid hormones via biotransformations, chemical synthesis or biotechnological production.

Hydrocortisone has a weak glucocorticoid effect and is a sought-after starting compound for the synthesis of active ingredients with a highly antiinflammatory, abortive or antiproliferative effect.

Squalene is used as building block for the synthesis of terpenes. In its hydrogenated form, it is used as squalane in dermatology and cosmetics, and in its various derivatives as constituent of skincare and haircare products.

Other economically utilizable substances are sterols, such as zymosterol and lanosterol, lanosterol being a pivotal raw material and synthetic material for the chemical synthesis of saponins and steroid hormones. Owing to its good skin penetration and spreading properties, lanosterol is used as emulsion auxiliary and active ingredient for skin creams.

An economical method for the production of ergosta-5,7-dienol and/or its biosynthetic intermediates and/or metabolites is therefore of great importance.

Methods which are particularly economical are biotechnological methods exploiting natural organisms or organisms optimized by means of genetic modification which produce ergosta-5,7-dienol and/or its biosynthetic intermediates and/or metabolites.

The genes of the ergosterol metabolism in yeast are largely known and cloned, such as, for example, nucleic acids encoding an HMG-CoA reductase (HMG) (Bason M. E. et al, (1988) Structural and functional conservation between yeast and human 3-hydroxy-3-methylglutaryl coenzyme A reductases, the rate-limiting enzyme of sterol biosynthesis. Mol Cell Biol 8:3797-3808, the nucleic acid encoding a truncated HMG-CoA reductase (t-HMG)(Polakowski T, Stahl U, Lang C. (1998) Overexpression of a cytosolic hydroxymethylglutaryl-CoA reductase leads to squalene accumulation in yeast. Appl Microbiol Biotechnol. January; 49(1):66-71, the nucleic acid encoding a lanosterol C14-demethylase (ERG11) (Kalb V F, Loper J C, Dey C R, Woods C W, Sutter T R (1986) Isolation of a cytochrome P-450 structural gene from *Saccharomyces cerevisiae*. Gene 45(3):237-45, the nucleic acid encoding a squalene epoxidase (ERG1) (Jandrositz, A., et al (1991) The gene encoding squalene epoxidase from *Saccharomyces cerevisiae*: cloning and characterization. Gene 107:155-160 and nucleic acids encoding a squalene synthetase (ERG9) (Jennings, S. M., (1991): Molecular cloning and characterization of the yeast gene for squalene synthetase. Proc Natl Acad Sci USA. July 15; 88(14):6038-42).

There are furthermore known processes which aim at increasing the content in specific intermediates and catabolites of the sterol metabolism in yeasts and fungi.

It is known from T. Polakowski, Molekularbiologische Beeinflussung des Ergosterolstoffwechsels der Hefe *Saccharomyces cerevisiae* [Molecular-biological effects on the ergosterol metabolism of the yeast *Saccharomyces cerevisiae*], Shaker Verlag Aachen, 1999, pages 59 to 66, that increasing the expression rate of HMG-CoA reductase leads to a slightly increased content in early sterols, such as squalene, while the content in later sterols, such as ergosterol, does not change significantly or even has a tendency to decrease.

Tainaka et al., J, Ferment. Bioeng. 1995, 79, 64-66 furthermore describe that the overexpression of ERG11 (lanosterol C14-demethylase) leads to the accumulation of 4,4-dimethylzymosterol, but not ergosterol. In comparison with the wild type, the zymosterol content of the transformant is increased by a factor of 1.1 to 1.47, depending on the fermentation conditions.

WO 99/16886 describes a method for the production of ergosterol in yeasts which overexpress a combination of the genes tHMG, ERG9, SAT1 and ERG1.

EP 486 290 discloses a method for increasing the squalene, zymosterol, ergosta-5,7,-24(28)-trienol and ergosta-5,7-dienol content in yeast by increasing the HMG-CoA reductase expression rate and simultaneously interrupting the metabolic pathway of ergosta-5,7,24(28)-trienol-22-dehydrogenase, hereinbelow also referred to as Δ22-desaturase (ERG5).

However, the disadvantage of this method is that the ergosta-5,7-dienol yield is still not satisfactory.

It is an object of the present invention to provide a further method for the production of ergosta-5,7-dienol and/or its biosynthetic intermediates and/or metabolites with advantageous characteristics, such as a higher product yield.

Figure 1:
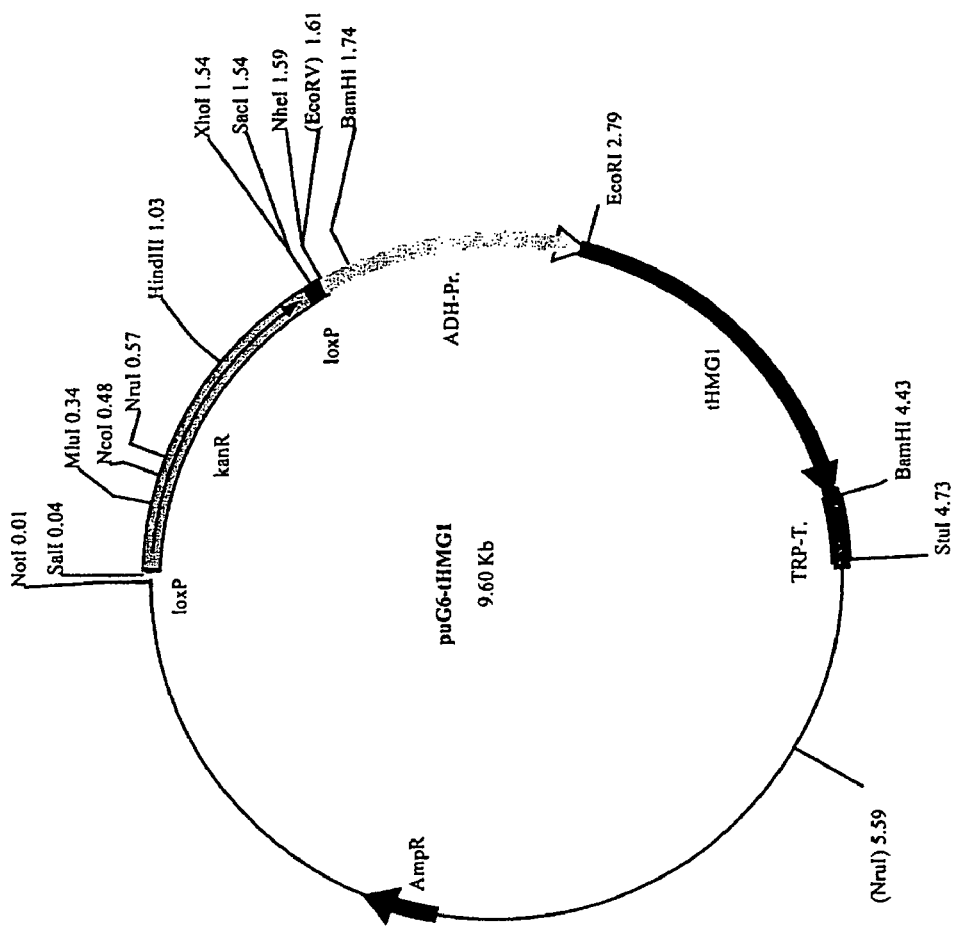
FIG. 1 shows vector pUG6 tHMG.

We have found that this object is achieved by a method for producing ergosta-5,7-dienol and/or its biosynthetic intermediates and/or metabolites in which organisms are cultured which have a reduced Δ22-desaturase activity and an increased HMG-CoA reductase activity and an increased activity of at least one of the activities selected from the group consisting of lanosterol C14-demethylase activity, squalene epoxidase activity and squalene synthetase activity in comparison with the wild type.

A reduced activity is understood as meaning not only the reduction of the activity, but also the complete elimination of the activity. Accordingly, a reduction of an activity also encompasses a quantitative reduction of the relevant protein in the organism through to a complete absence of the relevant protein, which can be assayed, for example, by a lack of detectability of the relevant enzyme activity or a lack of immunological detectability of the relevant proteins.

Δ22-desaturase activity is understood as meaning the enzyme activity of a Δ22-desaturase.

A Δ22-desaturase is understood as meaning a protein with the enzymatic activity of converting ergosta-5,7-dienol into ergosta-5,7,22,24-tetraen-3β-ol.

Accordingly, Δ22-desaturase activity is understood as meaning the amount of ergosta-5,7-dienol converted, or the amount of ergosta-5,7,22,24-tetraen-3β-ol formed, by the protein Δ22-desaturase within a specific period of time.

Thus, in the case of reduced Δ22-desaturase activity in comparison with the wild type, the amount of ergosta-5,7-dienol converted, or the amount of ergosta-5,7,22,24-tetraen-3β-ol formed, by the protein Δ22-desaturase within a specific period of time is reduced in comparison with the wild type.

The Δ22-desaturase activity is preferably reduced to at least 90%, more preferably to at least 70%, more preferably to at least 50%, more preferably to at least 30%, even more preferably by at least 10%, even more preferably by at least 5%, in particular to 0% of the Δ22-desaturase activity of the wild type. Especially preferred is, accordingly, the elimination of the Δ22-desaturase activity in the organism.

The Δ22-desaturase (ERG5) activity can be determined as described hereinbelow:

Various concentrations of ergosta-5,7-dienol, isolated from *S. cerevisiae* Erg5 mutants (Parks et al, 1985. Yeast sterols.yeast mutants as tools for the study of sterol metabolism. Methods Enzymol. 111:333-346) and 50 μg of dilauroylphosphatidylcholin are mixed and sonicated until a white suspension forms. Processed microsomes are added (1 ml)(3 mg/ml protein). NADPH (final concentration 1 mM) is added to the test mixture in order to start the enzyme reaction. The mixture is incubated for 20 minutes at 37° C. The reaction is stopped by addition of 3 ml of methanol, and sterols are hydrolyzed by addition of 2 ml 60% (wt/vol) KOH in water. The mixture is incubated for 2 hours at 90° C. After cooling, the mixture is extracted three times with 5 ml of hexane and concentrated by evaporation on a rotary evaporator. The sterols are subsequently silylated with bis(trimethylsilyl)trifluoroacetamide (50 μl in 50 μl of toluene) for one hour at 60° C. The sterols are analyzed by gas chromatography/mass spectroscopy (GC-MS) (for example Model VG 12-250 gas chromatograph-mass spectrometer; VG Biotech, Manchester, United Kingdom). The resulting Δ22-desaturated intermediate can be identified as a function of the amount of substrate employed. Microsomes which are not incubated with substrate act as reference.

This method is a modification of the method described in Lamb et al: Purification, reconstitution, and inhibition of cytochrome P-450 sterol delta22-desaturase from the pathogenic fungus *Candida glabrata*. Antimicrob Agents Chemother. 1999 July; 43(7):1725-8.

The Δ22-desaturase activity can be reduced independently by different cytological mechanisms, for example by inhibiting the corresponding activity at the protein level, for example by addition of inhibitors of the enzymes in question, or by reducing the gene expression of the corresponding nucleic acids encoding a Δ22-desaturase in comparison with the wild type.

In a preferred embodiment of the method according to the invention, the Δ22-desaturase activity is reduced in comparison with the wild type by reducing the gene expression of the corresponding nucleic acids encoding a Δ22-desaturase.

Reducing the gene expression of the nucleic acids encoding a Δ22-desaturase in comparison with the wild type can likewise be effected in various ways, for example by a) introducing nucleic acid sequences which can be transcribed into an antisense nucleic acid sequence which is capable of inhibiting the Δ22-desaturase activity, for example by inhibiting the expression of endogenous Δ22-desaturase activity, b) overexpressing homologous Δ22-desaturase nucleic acid sequences, which lead to cosuppression, c) introducing nonsense mutations into the endogen by introducing RNA/DNA oligonucleotides into the organism, d) introducing specific DNA-binding factors, for example factors of the zinc finger transcription factor type, which bring about a reduced gene expression, or e) generating knock-out mutants, for example with the aid of T-DNA mutagenesis or homologous recombination.

In a preferred embodiment of the method according to the invention, the gene expression of the nucleic acids encoding a Δ22-desaturase is reduced by generating knock-out mutants, especially preferably by homologous recombination.

Accordingly, it is preferred to use an organism without a functional Δ22-desaturase gene.

In a preferred embodiment, the generation of knock-out mutants, that is to say the deletion of the target locus Δ22-desaturase gene, is carried out simultaneously with the integration of an expression cassette comprising at least one of the nucleic acids described hereinbelow, encoding a protein whose activity is being increased in comparison with the wild type, by homologous recombination.

To this end, it is possible to use nucleic acid constructs which, in addition to the expression cassettes described hereinbelow comprising promoter, coding sequence and, if appropriate, terminator, and in addition to a selection marker described hereinbelow, comprise, at the 3' and 5' end, nucleic acid sequences which are identical to nucleic acid sequences at the beginning and at the end of the gene to be deleted.

Once selection has taken place, it is preferred to remove the selection marker again by means of recombinase systems, for example by loxP signals at the 3' and 5' end of the selection marker, using a Cre recombinase (Cre-LoxP system).

In the preferred organism *Saccharomyces cerevisiae*, the Δ22-desaturase gene denotes the gene ERG5 (SEQ. ID. NO. 1). SEQ. ID. NO. 2 constitutes the corresponding *Saccharomyces cerevisiae* Δ22-desaturase (Skaggs, B. A. et al,: Cloning and characterization of the *Saccharomyces cerevisiae* C-22 sterol desaturase gene, encoding a second cytochrome P-450 involved in ergosterol biosynthesis, Gene. 1996 Feb. 22; 169(1):105-9.).

HMG-CoA reductase activity is understood as meaning the enzyme activity of an HMG-CoA reductase (3-hydroxy-3-methylglutaryl-coenzyme A reductase).

An HMG-CoA reductase is understood as meaning a protein with the enzymatic activity of converting 3-hydroxy-3-methylglutaryl-coenzyme A into mevalonate.

Accordingly, HMG-CoA reductase activity is understood as meaning the amount of 3-hydroxy-3-methylglutaryl-coenzyme A converted, or the amount of mevalonate formed, by the protein HMG-CoA reductase within a specific period of time.

Thus, in the case of an increased HMG-CoA reductase activity in comparison with the wild type, the amount of 3-hydroxy-3-methylglutaryl-coenzyme A converted, or the amount of mevalonate formed, by the protein HMG-CoA reductase within a specific period of time is increased in comparison with the wild type.

Preferably, this increase in the HMG-CoA reductase activity amounts to at least 5%, more preferably to at least 20%, more preferably to at least 50%, more preferably to at least 100%, even more preferably to at least 300%, especially preferably to at least 500%, in particular to at least 600% of the HMG-CoA reductase activity of the wild type.

The HMG-CoA reductase activity is determined as described in Th. Polakowski, Molekularbiologische Beeinflussung des Ergosterolstoffwechsels der Hefe *Saccharomyces cerevisiae*, Shaker-Verlag, Aachen 1999, ISBN 3-8265-6211-9.

According to this reference, $10^9$ yeast cells of a 48-hour-old culture are harvested by centrifugation (3500×g, 5 min) and washed in 2 ml of buffer I (100 mM potassium phosphate buffer, pH 7.0). The cell pellet is taken up in 500 µl of buffer 1 (cytosolic proteins) or 2 (100 mM potassium phosphate buffer pH7.0; 1% Triton X-100) (total proteins), and 1 µl of 500 mM PMSF in isopropanol is added. 500 µl of glass beads (d=0.5 mm) are added to the cells, and the cells are disrupted by vortexing 5× for one minute. The liquid between the glass beads is transferred into a fresh Eppendorf tube. Cell debris and membrane components are removed by centrifuging for 15 minutes (14000×g). The supernatant is transferred into a fresh Eppendorf tube and constitutes the protein fraction.

The HMG-CoA activity is determined by measuring the consumption of NADPH+H$^+$ in the reduction of 3-hydroxy-3-methylglutaryl-CoA, which is added as a substrate.

In a reaction volume of 1000 µl there are added 20 µl of yeast protein isolate together with 910 µl of buffer I; 50 µl of 0.1 M DTT and 10 µl of 16 mM NADPH+H$^+$. The reaction mixture is warmed to 30° C. and is measured in a photometer for 7.5 minutes at 340 nm. The decrease in NADPH which is measured during this period is the breakdown rate without added substrate and is taken into consideration as background.

Thereafter, substrate is added (10 µl of 30 mM HMG-CoA), and the measurement is continued for 7.5 minutes. The HMG-CoA reductase activity is calculated by determining the specific NADPH breakdown rate.

Lanosterol C14-demethylase activity is understood as meaning the enzyme activity of a lanosterol C14-demethylase.

A lanosterol C14-demethylase is understood as meaning a protein with the enzymatic activity of converting lanosterol into 4,4-dimethylcholesta-8,14,24-trienol.

Accordingly, lanosterol C14-demethylase activity is understood as meaning the amount of lanosterol converted, or the amount of 4,4-dimethylcholesta-8,14,24-trienol formed, by the protein lanosterol C14-demethylase within a specific period of time.

Thus, in the case of an increased lanosterol C14-demethylase activity in comparison with the wild type, the amount of lanosterol converted, or the amount of 4,4-dimethylcholesta-8,14,24-trienol formed, by the protein lanosterol C14-demethylase within a specific period of time is increased in comparison with the wild type.

Preferably, this increase in the lanosterol C14-demethylase activity amounts to at least 5%, more preferably to at least 20%, more preferably to at least 50%, more preferably to at least 100%, even more preferably to at least 300%, especially preferably to at least 500%, in particular to at least 600%, of the lanosterol C14-demethylase activity of the wild type.

The lanosterol C14-demethylase activity is determined as described in Omura, T and Sato, R. (1964) The carbon monoxide binding pigment in liver microsomes. J. Biol. Chem. 239, 2370-2378. In this test, the amount of P450 enzyme is semiquantifiable as the holoenzyme with bound heme. The (active) holoenzyme (with heme) can be reduced by CO, and only the CO-reduced enzyme has an absorption maximum at 450 nm. Thus, the absorption maximum at 450 nm is a measure for the lanosterol C14-demethylase activity.

To carry out the activity determination, a microsome fraction (4-10 mg/ml protein in 100 mM potassium phosphate buffer) is diluted 1:4 in such a way that the protein concentration employed for the assay is 2 mg/ml. The assay is carried out directly in a cell.

A spatula-tipful of dithionite ($S_2O_4Na_2$) is added to the microsomes. The baseline is recorded with a spectrophotometer in the 380-500 nm range.

Approximately 20-30 CO bubbles are subsequently bubbled through the sample. The absorption is now measured in the same range. The absorption level at 450 nm corresponds to the amount of P450 enzyme in the reaction mixture.

Squalene epoxidase activity is understood as meaning the enzyme activity of a squalene epoxidase.

A squalene epoxidase is understood as meaning a protein with the enzymatic activity of converting squalene into squalene epoxide.

Accordingly, squalene epoxidase activity is understood as meaning the amount of squalene converted, or the amount of squalene epoxide formed, by the protein squalene epoxidase within a specific period of time.

Thus, in the case of an increased squalene epoxidase activity in comparison with the wild type, the amount of squalene converted, or the amount of squalene epoxide formed, by the protein squalene epoxidase within a specific period of time is increased in comparison with the wild type.

Preferably, this increase in squalene epoxidase activity amounts to at least 5%, more preferably to at least 20%, more preferably to at least 50%, more preferably to at least 100%, even more preferably to at least 300%, especially preferably to at least 500%, in particular to at least 600% of the squalene epoxidase activity of the wild type.

The squalene epoxidase activity is determined as described in Leber R, Landl K, Zinser E, Ahorn H, Spok A, Kohlwein S D, Turnowsky F, Daum G. (1998) Dual localization of squalene epoxidase, Erg1p, in yeast reflects a relationship between the endoplasmic reticulum and lipid particles, Mol. Biol. Cell. 1998, February; 9(2):375-86.

This method comprises 0.35 to 0.7 mg of microsomal protein or 3.5 to 75 µg of lipid particle protein in 100 mM Tris-HCl, pH 7.5, 1 mM EDTA, 0.1 mM FAD, 3 mM NADPH, 0.1 mM squalene 2,3-epoxidase cyclase inhibitor U18666A, 32 µM [$^3$H]squalene dispersed in 0.005% Tween 80 in a total volume of 500 µl.

The assay is carried out at 30° C. After pretreatment for 10 minutes, the reaction is started by addition of squalene and stopped after 15, 30 or 45 minutes by lipid extraction with 3 ml of chloroform/methanol (2:1 vol/vol) and 750 µl 0.035% $MgCl_2$.

The lipids are dried under nitrogen and redissolved in 0.5 ml of chloroform/methanol (2:1 vol/vol). For a thin-layer chromatography, portions are placed on a silica gel 60 plate (0.2 mm) and separated with chloroform as the eluant. The positions containing [$^3$H]2,3-oxidosqualene and [$^3$H] squalene were scraped out and quantified with a scintillation counter.

Squalene synthetase activity is understood as meaning the enzyme activity of a squalene synthetase.

Squalene synthetase is understood as meaning a protein with the enzymatic activity of converting farnesyl pyrophosphate into squalene.

Accordingly, squalene synthetase activity is understood as meaning the amount of farnesyl pyrophosphate converted, or the amount of squalene formed, by the protein squalene synthetase within a specific period of time.

Thus, in the case of an increased squalene synthetase activity in comparison with the wild type, the amount of farnesyl pyrophosphate converted, or the amount of squalene formed, by the protein squalene synthetase within a specific period of time is increased in comparison with the wild type.

Preferably, this increase in squalene synthetase activity amounts to at least 5%, more preferably to at least 20%, more preferably to at least 50%, more preferably to at least 100%, even more preferably to at least 300%, especially preferably to at least 500%, in particular to at least 600% of the squalene synthetase activity of the wild type.

The squalene synthetase activity can be determined as described hereinbelow:

The reaction mixtures comprise 50 mM Mops, pH 7.2, 10 mM $MgCl_2$, 1% (v/v) Tween-80, 10% (v/v) 2-propanol, 1 mM DTT, 1 mg/ml BSA, NADPH, FPP (or PSPP) and microsomes (protein content 3 mg) in a total volume of 200 µl in glass tubes. Reactions with radioactive substrate [1-$^3$H] FPP (15-30 mCi/µmol) are incubated for 30 minutes at 30° C., and the suspension mixture is filled up with 1 volume of 1:1 (v/v) 40% aqueous KOH:methanol. Liquid NaCl is added until the solution is saturated, and 2 ml of ligroin comprising 0.5% (v/v) squalene are likewise added.

The suspension is vortexed for 30 seconds. Using a Pasteur pipette, 1 ml portions of the ligroin layer are applied to a packed 0.5×6 cm aluminum column (80-200 mesh, Fisher). The column is preequilibrated with 2 ml of ligroin comprising 0.5% (v/v) squalene. The column is subsequently eluted with 5×1 ml toluene comprising 0.5% (v/v) squalene. The squalene radioactivity is measured in Cytoscint (ICN) scintillation cocktail using a scintillation counter (Beckman).

This method is a modification of the methods described in Radisky et al., Biochemistry. 2000 Feb. 22; 39(7):1748-60, Zhang et al. (1993) *Arch. Biochem. Biophys.* 304, 133-143 and Poulter, C. D. et al. (1989) *J. Am. Chem. Soc.* 111, 3734-3739.

A wild type is understood as meaning the corresponding non-genetically-modified starting organism. Preferably, and in particular in cases where the organism or the wild type are not unambiguously identifiable, the wild type for the reduction of the Δ22-desaturase activity, the increase in the HMG-CoA reductase activity, the increase in the lanosterol C14-demethylase activity, the increase in the squalene epoxidase activity and the increase in the squalene synthetase activity, and for the increase in the content in ergosta-5,7-dienol and/or its biosynthetic intermediates and/or metabolites is understood as meaning a reference organism. This reference organism is preferably the yeast strain *Saccharomyces cerevisiae* AH22.

The HMG-CoA reductase activity, the lanosterol C14-demethylase activity, the squalene epoxidase activity or the squalene synthetase activity can be increased independently in various ways, for example by eliminating inhibiting regulatory mechanisms at the expression and protein level, or by increasing the gene expression of the corresponding nucleic acids, that is to say nucleic acids encoding an HMG-CoA reductase, lanosterol C14-demethylase, squalene epoxidase or squalene synthetase, in comparison with the wild type.

Increasing the gene expression of the corresponding nucleic acid in comparison with the wild type can likewise be effected in various ways, for example by inducing the corresponding genes by activators, that is to say by inducing the HMG-CoA reductase gene, the lanosterol C14-demethylase gene, the squalene epoxidase gene or the squalene synthetase gene by activators or by introducing one or more gene copies of the corresponding nucleic acids, that is to say by introducing, into the organism, one or more nucleic acids encoding an HMG-CoA reductase, lanosterol C14-demethylase, squalene epoxidase or squalene synthetase.

In accordance with the invention, increasing the gene expression of a nucleic acid encoding an HMG-CoA reductase, lanosterol C14-demethylase, squalene epoxidase or squalene synthetase is also understood as meaning the manipulation of the expression of the organism's own, in particular the yeast's own, endogenous HMG-CoA reductases, lanosterol C14-demethylases, squalene epoxidases or squalene synthetases.

This can be achieved for example by modifying the promoter DNA sequence for genes encoding HMG-CoA reductase, lanosterol C14-demethylase, squalene epoxidase or squalene synthetase. Such a modification, which results in an increased expression rate of the gene in question, can be brought about for example by deletion or insertion of DNA sequences.

As described above, it is possible to modify the expression of the endogenous HMG-CoA reductase, lanosterol C14-demethylase, squalene epoxidase or squalene synthetase by applying exogenous stimuli. This can be brought about by specific physiological conditions, that is to say by the application of foreign substances.

Moreover, a modified or increased expression of endogenous HMG-CoA reductase, lanosterol C14-demethylase, squalene epoxidase or squalene synthetase genes can be achieved by a regulator protein which does not occur in the nontransformed organism interacts with the promoter of these genes.

Such a regulator may be a chimeric protein consisting of a DNA binding domain and a transcription activator domain, as described, for example, in WO 96/06166.

In a preferred embodiment, the increase in lanosterol C14-demethylase activity in comparison with the wild type is effected by increasing the gene expression of a nucleic acid encoding a lanosterol C14-demethylase.

In a furthermore preferred embodiment, the increase in the gene expression of a nucleic acid encoding a lanosterol C14-demethylase is effected by introducing, into the organism, one or more nucleic acids encoding a lanosterol C14-demethylase.

In principle, any lanosterol C14-demethylase gene (ERG11), that is to say any nucleic acid encoding a lanosterol C14-demethylase, may be used for this purpose. In the case of genomic lanosterol C14-demethylase nucleic acid sequences from eukaryotic sources, which contain introns, and in the event that the host organism is not capable, or cannot be made capable, of expressing the corresponding lanosterol C14-demethylase, it is preferred to use preprocessed nucleic acid sequences, such as the corresponding cDNAs.

Examples of lanosterol C14-demethylase genes are nucleic acids encoding a lanosterol C14-demethylase from *Saccharomyces cerevisiae* (Kalb V F, Loper J C, Dey C R, Woods C W, Sutter T R (1986) Isolation of a cytochrome P-450 structural gene from *Saccharomyces cerevisiae*. Gene 45(3):237-45), *Candida albicans* (Lamb D C, Kelly D E, Baldwin B C, Gozzo F, Boscott P, Richards W G, Kelly S L (1997) Differential inhibition of *Candida albicans* CYP51 with azole antifungal stereoisomers. FEMS Microbiol Lett 149(1):25-30), *Homo sapiens* (Stromstedt M, Rozman D, Waterman M R. (1996) The ubiquitously expressed human CYP51 encodes lanosterol 14 alpha-demethylase, a cytochrome P450 whose expression is regulated by oxysterols. Arch Biochem Biophys 1996 May 1; 329(1):73-81c) or *Rattus norvegicus*, Aoyama Y, Funae Y, Noshiro M, Horiuchi T, Yoshida Y. (1994) Occurrence of a P450 showing high homology to yeast lanosterol 14-demethylase (P450(14DM)) in the rat liver. Biochem Biophys Res Commun. June 30; 201(3):1320-6).

In the transgenic organisms according to the invention, there thus exists, in this preferred embodiment, at least one further lanosterol C14-demethylase gene in comparison with the wild type.

The number of the lanosterol C14-demethylase genes in the transgenic organisms according to the invention is at least two, preferably more than two, especially preferably more than three, very especially preferably more than five.

All of the nucleic acids mentioned in the description may be, for example, an RNA, DNA or cDNA sequence.

The above-described method preferably employs nucleic acids encoding proteins comprising the amino acid sequence SEQ. ID. NO. 6 or a sequence derived from this sequence by substitution, insertion or deletion of amino acids which has at least 30%, preferably at least 50%, more preferably at least 70%, especially preferably at least 90%, most preferably at least 95% identity with the sequence SEQ. ID. NO. 6 at the amino acid level, which proteins have the enzymatic characteristic of a lanosterol C14-demethylase.

The sequence SEQ. ID. NO. 6 constitutes the amino acid sequence of the *Saccharomyces cerevisiae* lanosterol C14-demethylase.

Further examples of lanosterol C14-demethylases and lanosterol C14-demethylase genes can be found readily, for example from various organisms whose genomic sequence is known, by homology comparisons of the amino acid sequences or of the corresponding backtranslated nucleic acid sequences from databases with SEQ. ID. NO. 2.

Further examples of lanosterol C14-demethylases and lanosterol C14-demethylase genes can be found readily in a manner known per se by hybridization and PCR techniques from various organisms whose genomic sequence is not known, for example starting from the sequence SEQ. ID. NO. 5.

In the description, the term "substitution" is understood as meaning the substitution of one or more amino acids by one or more amino acids. It is preferred to perform what are known as conservative substitutions, in which the replacement amino acid has a similar property to the original amino acid, for example the substitution of Glu by Asp, Gln by Asn, Val by Ile, Leu by Ile, Ser by Thr.

Deletion is the replacement of an amino acid by a direct bond. Preferred positions for deletions are the termini of the polypeptide and the linkages between the individual protein domains.

Insertions are introductions of amino acids into the polypeptide chain, a direct bond formally being replaced by one or more amino acids.

Identity between two proteins is understood as meaning the identity of the amino acids over in each case the entire protein length, in particular the identity calculated by alignment with the aid of the Lasergene software from DNASTAR, inc. Madison, Wis. (USA) using the Clustal method (Higgins D G, Sharp P M. Fast and sensitive multiple sequence alignments on a microcomputer. Comput Appl. Biosci. 1989 April; 5(2): 151-1), setting the following parameters:
Multiple alignment parameter:
Gap penalty 10
Gap length penalty 10
Pairwise alignment parameter:
K-tuple 1
Gap penalty 3
Window 5
Diagonals saved 5

Accordingly, a protein with an identity of at least 30% with the sequence SEQ. ID. NO. 6 at the amino acid level is understood as meaning a protein which has at least 30% identity when its sequence is aligned with the sequence SEQ. ID. NO. 6, in particular in accordance with the above program algorithm with the above parameter set.

In a furthermore preferred embodiment, nucleic acids encoding proteins comprising the amino acid sequence of the *Saccharomyces cerevisiae* lanosterol C14-demethylase (SEQ. ID. NO. 6) are introduced into organisms.

Suitable nucleic acid sequences can be obtained for example by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in yeast, it is frequently advantageous to use the yeast codon usage when backtranslating.

In an especially preferred embodiment, a nucleic acid comprising the sequence SEQ. ID. NO. 5 is introduced into the organism.

The sequence SEQ. ID. NO. 5 constitutes the genomic DNA from *Saccharomyces cerevisiae* (ORF S0001049), which encodes the lanosterol C14-demethylase with the sequence SEQ ID NO. 6.

All of the abovementioned lanosterol C14-demethylase genes can furthermore be generated from the nucleotide units by chemical synthesis in a manner known per se, such as, for example, by fragment condensation of individual overlapping complementary nucleic acid units of the double helix. Oligonucleotides can be synthesized chemically for example in a known manner using the phosphoamidite method (Voet, Voet, 2nd Edition, Wiley Press New York, pages 896-897). The annealment of synthetic oligonucleotides and the filling in of gaps with the aid of the DNA polymerase Klenow fragment and ligation reactions are described in Sambrook et al. (1989), Molecular cloning: A laboratory manual, Cold Spring Harbor Laboratory Press, as are general cloning methods.

In a preferred embodiment, increasing the HMG-CoA reductase activity in comparison with the wild type is effected by increasing the gene expression of a nucleic acid encoding an HMG-CoA reductase.

In an especially preferred embodiment of the method according to the invention, increasing the gene expression of a nucleic acid encoding an HMG-CoA reductase is effected by introducing, into the organism, a nucleic acid construct comprising a nucleic acid encoding an HMG-CoA reductase whose expression in the organism is subject to reduced regulation in comparison with the wild type.

Reduced regulation in comparison with the wild type is understood as meaning a regulation which is reduced in comparison with the above-defined wild type, preferably no regulation, at the expression or protein level.

The reduced regulation can preferably be achieved by means of a promoter which is operably linked to the coding sequence in the nucleic acid construct and which, in the organism, is subject to reduced regulation in comparison with the wild-type promoter.

For example, the middle ADH promoter in yeast is only subject to reduced regulation and is therefore particularly preferred as promoter in the above-described nucleic acid construct.

This promoter fragment of the ADH12s promoter, hereinbelow also referred to as ADH1, shows almost constitutive expression (Ruohonen L, Penttila M, Keranen S. (1991) Optimization of *Bacillus* alpha-amylase production by *Saccharo-*

*myces cerevisiae*. Yeast. May-June; 7(4):337-462; Lang C, Looman A C. (1995) Efficient expression and secretion of *Aspergillus niger* RH5344 polygalacturonase in *Saccharomyces cerevisiae*. Appl Microbiol Biotechnol. December; 44(1-2):147-56.), so that the transcriptional regulation no longer proceeds via ergosterol biosynthesis intermediates.

Further preferred promoters with reduced regulation are constitutive promoters such as, for example, the yeast TEF1 promoter, the yeast GPD promoter or the yeast PGK promoter (Mumberg D, Muller R, Funk M. (1995) Yeast vectors for the controlled expression of heterologous proteins in different genetic backgrounds. Gene. 1995 Apr. 14; 156(1):119-22; Chen C Y, Oppermann H, Hitzeman R A. (1984) Homologous versus heterologous gene expression in the yeast, *Saccharomyces cerevisiae*. Nucleic Acids Res. December 11; 12(23): 8951-70.).

In a further preferred embodiment, reduced regulation can be achieved by using, as the nucleic acid encoding an HMG-CoA reductase, a nucleic acid whose expression in the organism is subject to reduced regulation in comparison with the homologous, orthologous nucleic acid.

It is especially preferred to use a nucleic acid which only encodes the catalytic region of the HMG-CoA reductase (truncated (t-)HMG-CoA reductase) as the nucleic acid encoding an HMG-CoA reductase. This nucleic acid (t-HMG), which is described in EP 486 290 and WO 99/16886, only encodes the catalytically active portion of the HMG-CoA reductase while the membrane domain, which is responsible for the regulation at the protein level, is absent. Thus, this nucleic acid is subjected to reduced regulation, in particular in yeast, and leads to an increased gene expression of the HMG-CoA reductase.

The above-described nucleic acid construct can be incorporated into the host organism either chromosomally using integration vectors or episomally using episomal plasmids, in each case comprising the above-described nucleic acid construct.

In an especially preferred embodiment, nucleic acids are introduced, preferably via the above-described nucleic acid construct, which encode proteins comprising the amino acid sequence SEQ. ID. NO. 4 or a sequence derived from this sequence by substitution, insertion or deletion of amino acids which has at least 30% identity with the sequence SEQ. ID. NO. 4 at the amino acid level, which proteins have the enzymatic characteristic of an HMG-CoA reductase.

The sequence SEQ. ID. NO. 4 constitutes the amino acid sequence of the truncated HMG-CoA reductase (t-HMG).

Further examples of HMG-CoA reductases, and thus also of the t-HMG-CoA reductases which are reduced to the catalytic portion, or the coding genes, can be found readily, for example from various organisms whose genomic sequence is known, by homology comparisons of the amino acid sequences or of the corresponding back-translated nucleic acid sequences from databases with SEQ ID. NO. 4.

Further examples of HMG-CoA reductases, and thus also of the t-HMG-CoA reductases which are reduced to the catalytic portion, or the coding genes, can be found readily from various organisms whose genomic sequence is not known by hybridization and PCR techniques in a manner known per se, for example starting from the sequence SEQ. ID. No. 3.

It is especially preferred to use a nucleic acid comprising the sequence SEQ. ID. NO. 3 as nucleic acid encoding a truncated HMG-CoA reductase.

In an especially preferred embodiment, the reduced regulation is achieved by using, as nucleic acid encoding an HMG-CoA reductase, a nucleic acid whose expression in the organism is subject to reduced regulation in comparison with the organism's own, orthologous nucleic acid and by using a promoter which is subject to reduced regulation in the organism in comparison with the wild-type promoter.

In a preferred embodiment, increasing the squalene epoxidase activity in comparison with the wild type is effected by increasing the gene expression of a nucleic acid encoding a squalene epoxidase.

In a furthermore preferred embodiment, increasing the gene expression of a nucleic acid encoding a squalene epoxidase is effected by introducing, into the organism, one or more nucleic acids encoding squalene epoxidase.

In principle, any squalene epoxidase gene (ERG1), that is to say any nucleic acid which encodes a squalene epoxidase, may be used for this purpose. In the case of genomic squalene epoxidase nucleic acid sequences from eukaryotic sources, which contain introns, and in the event that the host organism is not capable, or cannot be made capable, of expressing the corresponding squalene epoxidase, it is preferred to use preprocessed nucleic acid sequences, such as the corresponding cDNAs.

Examples of nucleic acids encoding a squalene epoxidase are nucleic acids encoding a squalene epoxidase from *Saccharomyces cerevisiae* (Jandrositz, A., et al (1991) The gene encoding squalene epoxidase from *Saccharomyces cerevisiae*: cloning and characterization. Gene 107:155-160, from *Mus musculus* (Kosuga K, Hata S, Osumi T, Sakakibara J, Ono T. (1995) Nucleotide sequence of a cDNA for mouse squalene epoxidase, Biochim Biophys Acta, February 21; 1260(3):345-8b), from *Rattus norvegicus* (Sakakibara J, Watanabe R, Kanai Y, Ono T. (1995) Molecular cloning and expression of rat squalene epoxidase. J Biol Chem January 6; 270(1):17-20c) or from *Homo sapiens* (Nakamura Y, Sakakibara J, Izumi T, Shibata A, Ono T. (1996) Transcriptional regulation of squalene epoxidase by sterols and inhibitors in HeLa cells., J. Biol. Chem. 1996, April 5; 271(14):8053-6).

In the transgenic organisms according to the invention, there thus exists, in this preferred embodiment, at least one further squalene epoxidase gene in comparison with the wild type.

The number of the squalene epoxidase genes in the transgenic organisms according to the invention is at least two, preferably more than two, especially preferably more than three, very especially preferably more than five.

The above-described method preferably employs nucleic acids encoding proteins comprising the amino acid sequence SEQ. ID. NO. 8 or a sequence derived from this sequence by substitution, insertion or deletion of amino acids which has at least 30%, preferably at least 50%, more preferably at least 70%, especially preferably at least 90%, most preferably at least 95% identity with the sequence SEQ. ID. NO. 8 at the amino acid level, which proteins have the enzymatic characteristic of a squalene epoxidase.

The sequence SEQ. ID. NO. 8 constitutes the amino acid sequence of the *Saccharomyces cerevisiae* squalene epoxidase.

Further examples of squalene epoxidases and squalene epoxidase genes can be found readily, for example from various organisms whose genomic sequence is known, by homology comparisons of the amino acid sequences or of the corresponding backtranslated nucleic acid sequences from databases with SEQ. ID. NO. 8.

Further examples of squalene epoxidase and squalene epoxidase genes can be found readily in a manner known per se by hybridization and PCR techniques from various organisms whose genomic sequence is not known, for example starting from the sequence SEQ. ID. NO. 7.

In a furthermore preferred embodiment, nucleic acids encoding proteins comprising the amino acid sequence of the *Saccharomyces cerevisiae* squalene epoxidase (SEQ. ID. NO. 8) are introduced into organisms.

Suitable nucleic acid sequences can be obtained for example by backtranslating the polypeptide sequence in accordance with the genetic code.

Codons which are preferably used for this purpose are those which are used frequently in accordance with the organism-specific codon usage. The codon usage can be determined readily with the aid of computer evaluations of other, known genes of the organisms in question.

If, for example, the protein is to be expressed in yeast, it is frequently advantageous to use the yeast codon usage when backtranslating.

In an especially preferred embodiment, a nucleic acid comprising the sequence SEQ. ID. NO. 7 is introduced into the organism.

The sequence SEQ. ID. NO. 7 constitutes the genomic DNA from *Saccharomyces cerevisiae* (ORF S0003407), which encodes the squalene epoxidase with the sequence SEQ ID NO. 8.

All of the abovementioned squalene epoxidase genes can furthermore be generated from the nucleotide units by chemical synthesis in a manner known per se, such as, for example, by fragment condensation of individual overlapping complementary nucleic acid units of the double helix. Oligonucleotides can be synthesized chemically for example in a known manner using the phosphoamidite method (Voet, Voet, 2nd Edition, Wiley Press New York, pages 896-897). The annealment of synthetic oligonucleotides and the filling in of gaps with the aid of the DNA polymerase Klenow fragment and ligation reactions are described in Sambrook et al. (1989), Molecular cloning: A laboratory manual, Cold Spring Harbor Laboratory Press, as are general cloning methods.

In a preferred embodiment, increasing the squalene synthetase activity in comparison with the wild type is effected by increasing the gene expression of a nucleic acid encoding a squalene synthetase.

In a furthermore preferred embodiment, increasing the gene expression of a nucleic acid encoding a squalene synthetase is effected by introducing, into the organism, one or more nucleic acids encoding a squalene synthetase.

In principle, any squalene synthetase gene (ERG9), that is to say any nucleic acid which encodes a squalene synthetase, may be used for this purpose. In the case of genomic squalene synthetase nucleic acid sequences from eukaryotic sources, which contain introns, and in the event that the host organism is not capable, or cannot be made capable, of expressing the corresponding squalene synthetase, it is preferred to use preprocessed nucleic acid sequences, such as the corresponding cDNAs.

Examples of nucleic acids encoding a squalene synthetase are nucleic acids encoding a squalene synthetase from *Saccharomyces cerevisiae* (ERG9), (Jennings, S. M., (1991): Molecular cloning and characterization of the yeast gene for squalene synthetase. Proc Natl Acad Sci USA. July 15; 88(14):6038-42), nucleic acids encoding a squalene synthetase from *Botryococcus braunii* Okada (Devarenne, T. P. et al.: Molecular characterization of squalene synthase from the green microalga *Botryococcus braunii*, raceB, Arch. Biochem. Biophys. 2000, Jan. 15, 373(2):307-17), nucleic acids encoding a squalene synthetase from potato tuber (Yoshioka H. et al.: cDNA cloning of sesquiter penecyclase and squalene synthase, and expression of the genes in potato tuber infected with *Phytophthora infestans*, Plant. Cell. Physiol. 1999, September; 40(9):993-8) or nucleic acids encoding a squalene synthetase from *Glycyrrhiza glabra* (Hayashi, H. et al.: Molecular cloning and characterization of two cDNAs for *Glycyrrhiza glabra* squalene synthase, Biol. Pharm. Bull. 1999, September; 22(9):947-50).

In the transgenic organisms according to the invention, there thus exists, in this preferred embodiment, at least one further squalene synthetase gene in comparison with the wild type.

The number of the squalene synthetase genes in the transgenic organisms according to the invention is at least two, preferably more than two, especially preferably more than three, very especially preferably more than five.

The above-described method preferably employs nucleic acids encoding proteins comprising the amino acid sequence SEQ. ID. NO. 10 or a sequence derived from this sequence by substitution, insertion or deletion of amino acids which has at least 30%, preferably at least 50%, more preferably at least 70%, especially preferably at least 90%, most preferably at least 95% identity with the sequence SEQ. ID. NO. 10 at the amino acid level, which proteins have the enzymatic characteristic of a squalene synthetase.

The sequence SEQ. ID. NO. 10 constitutes the amino acid sequence of the *Saccharomyces cerevisiae* squalene synthetase (ERG9).

Further examples of squalene synthetases and squalene synthetase genes can be found readily, for example from various organisms whose genomic sequence is known, by homology comparisons of the amino acid sequences or of the corresponding backtranslated nucleic acid sequences from databases with SEQ. ID. NO. 10.

Further examples of squalene synthetases and squalene synthetase genes can be found readily in a manner known per se by hybridization and PCR techniques from various organisms whose genomic sequence is not known, for example starting from the sequence SEQ. ID. NO. 9.

In a furthermore preferred embodiment, nucleic acids encoding proteins comprising the amino acid sequence of the *Saccharomyces cerevisiae* squalene synthetase (SEQ. ID. NO. 10) are introduced into organisms.

Suitable nucleic acid sequences can be obtained for example by backtranslating the polypeptide sequence in accordance with the genetic code.

Codons which are preferably used for this prupose are those which are used frequently in accordance with the organism-specific codon usage. The codon usage can be determined readily with the aid of computer evaluations of other, known genes of the organisms in question.

If, for example, the protein is to be expressed in yeast, it is frequently advantageous to use the codon usage of yeast when backtranslating.

In an especially preferred embodiment, a nucleic acid comprising the sequence SEQ. ID. NO. 9 is introduced into the organism.

The sequence SEQ. ID. NO. 9 constitutes the genomic DNA from *Saccharomyces cerevisiae* (ORF YHR190W), which encodes the squalene synthetase of the sequence SEQ. ID. NO. 10.

All of the abovementioned squalene synthetase genes can furthermore be generated from the nucleotide units by chemical synthesis in a manner known per se, such as, for example, by fragment condensation of individual overlapping complementary nucleic acid units of the double helix. Oligonucleotides can be synthesized chemically for example in a known manner using the phosphoamidite method (Voet, Voet, 2nd Edition, Wiley Press New York, pages 896-897). The annealment of synthetic oligonucleotides and the filling in of gaps with the aid of the DNA polymerase Klenow fragment and ligation reactions are described in Sambrook et al. (1989), Molecular cloning: A laboratory manual, Cold Spring Harbor Laboratory Press, as are general cloning methods.

The organisms cultured in the method according to the invention are organisms which have a reduced Δ22-desaturase activity and an increased HMG-CoA reductase activity and an increased activity of at least one of the activities selected from the group consisting of lanosterol C14-demethylase activity, squalene epoxidase activity and squalene synthetase activity in comparison with the wild type.

In a preferred embodiment, the organisms cultured are organisms which have a reduced Δ22-desaturase activity and an increased HMG-CoA reductase activity and an increased lanosterol C14-demethylase activity, squalene epoxidase activity or squalene synthetase activity in comparison with the wild type.

In an especially preferred embodiment of the method according to the invention, the organisms have a reduced Δ22-desaturase activity and an increased HMG-CoA reductase activity and an increased activity of at least two of the activities selected from the group consisting of lanosterol C14-demethylase activity, squalene epoxidase activity and squalene synthetase activity in comparison with the wild type.

Especially preferred combinations are a reduced Δ22-desaturase activity and an increased HMG-CoA reductase activity and an increased lanosterol C14-demethylase activity and squalene epoxidase activity or lanosterol C14-demethylase activity and squalene synthetase activity or an increased squalene epoxidase activity and squalene synthetase activity in comparison with the wild type.

In a very especially preferred embodiment of the method according to the invention, the organisms have a reduced Δ22-desaturase activity and an increased HMG-CoA reductase activity and an increased lanosterol C14-demethylase activity and an increased squalene epoxidase activity and an increased squalene synthetase activity in comparison with the wild type.

Organisms or genetically modified organisms are understood as meaning, in accordance with the invention, for example bacteria, in particular bacteria of the genus *Bacillus, Escherichia coli, Lactobacillus* spec. or *Streptomyces* spec., for example yeasts, in particular yeasts of the genus *Saccharomyces cerevisiae, Pichia pastoris* or *Klyveromyces* spec., for example fungi, in particular fungi of the genus *Aspergillus* spec., *Penicillium* spec. or *Dictyostelium* spec., and, for example, also insect cell lines which are capable of generating ergosta-5,7-dienol and/or its biosynthetic intermediates and/or metabolites, either as the wild type or owing to preceding genetic modification.

Especially preferred organisms or genetically modified organisms are yeasts, in particular of the species *Saccharomyces cerevisiae*, in particular the yeast strains *Saccharomyces cerevisiae* AH22, *Saccharomyces cerevisiae* GRF, *Saccharomyces cerevisiae* DBY747 and *Saccharomyces cerevisiae* BY4741.

The biosynthetic intermediates of ergosta-5,7-dienol are understood as meaning all those compounds which occur as intermediates in the ergosta-5,7-dienol biosynthesis in the organism used, preferably the compounds mevalonate, farnesyl pyrophosphate, geraniol pyrophosphate, squalene epoxide, 4-dimethylcholesta-8,14,24-trienol, 4,4-dimethylzymosterol, squalene, farnesol, geraniol, lanosterol, zymosterone and zymosterol.

The biosynthetic metabolites of ergosta-5,7-dienol are understood as meaning all those compounds which are biosynthetic derivatives of ergosta-5,7-dienol in the organism used, that is to say in which ergosta-5,7-dienol occurs as intermediate. They may be compounds which the organism used produces naturally from ergosta-5,7-dienol.

However, they are also understood as meaning compounds which can only be produced from ergosta-5,7-dienol in the organism by introducing genes and enzyme activities from other organisms to which the starting organism has no orthologous gene.

Owing to the introduction of further plant genes and/or mammalian genes into yeast it is possible, for example, to produce biosynthetic ergosta-5,7-dienol metabolites which only occur naturally in plants and/or mammals in this yeast.

The introduction into yeast of, for example, nucleic acids encoding a plant Δ7-reductase (DWF5) or its functional equivalents or variants and of nucleic acids encoding mature forms of CYP11A1, ADX(FDX1), ADR (FDXR) and 3β-HSD or their functional equivalents or variants leads to the biosynthesis of progesterone in this yeast. A detailed description of the procedure and of the methods and materials for the corresponding genetic modification of yeast is published in C. Duport et al., Nat. Biotechnol. 1998, 16, 186-189 and in the references cited therein, which are herewith expressly incorporated by reference.

The introduction into yeast of, for example, nucleic acids encoding a plant Δ7-reductase (DWF5) or its functional equivalents or variants and of nucleic acids encoding mature forms of CYP11A1, ADX(FDX1) and ADR (FDXR) or their functional equivalents or variants and of nucleic acids encoding mitochondrial forms of ADX and CYP11B1, 3b-HSD, CYP17A1 and CYP21A1 or their functional equivalents or variants leads to the biosynthesis of hydrocortisone, 11-deoxycortisol, corticosterone and acetalpregnenolone.

To further increase the content in biosynthetic ergosta-5,7-dienol metabolites such as, for example, hydrocortisone, it is additionally advantageous to suppress wasteful metabolic pathways, that is to say biosynthetic pathways which do not lead to the desired product. For example, the reduction of the activities of the gene products of ATF2, GCY1 and YPR1, especially preferably the deletion of these activities, in yeast leads to a further increase in the hydrocortisone content.

A detailed description of this procedure and of the methods and materials for the corresponding genetic modification of yeast is published in F. M. Szczebara et al., Nat. Biotechnol. 2003, 21, 143-149 and in the references cited therein, which are herewith expressly incorporated by reference.

The biosynthetic ergosta-5,7-dienol metabolites are therefore understood as meaning in particular campesterol, pregnenolone, 17-OH pregnenolone, progesterone, 17-OH-progesterone, 11-deoxycortisol, hydrocortisone, deoxycorticosterone and/or corticosterone.

Preferred biosynthetic metabolites are progesterone, corticosterone and hydrocortisone, especially preferably hydrocortisone.

Some of the compounds produced in the method according to the invention are themselves steroid hormones and can be used for therapeutical purposes.

The compounds produced, such as, for example, ergosta-5,7-dienol or hydrocortisone, can furthermore be used for preparing steroid hormones or for the synthesis of active ingredients with a potent antiinflammatory, abortive or antiproliferative activity via biotransformation, chemical synthesis or biotechnological production.

In the method according to the invention for the production of ergosta-5,7-dienol and/or its biosynthetic intermediates and/or metabolites the step of culturing the genetically modified organisms, hereinbelow also referred to as transgenic organisms, is preferably followed by harvesting of the organisms and isolation of ergosta-5,7-dienol and/or its biosynthetic intermediates and/or metabolites from the organisms.

The organisms are harvested in a manner known per se to suit the organism in question. Microorganisms such as bacteria, mosses, yeasts and fungi or plant cells which are grown in liquid nutrient media by fermentation can be separated for example by centrifugation, decanting or filtration.

Ergosta-5,7-dienol and/or its biosynthetic intermediates and/or metabolites from the harvested biomass are isolated jointly or separately for each compound in a manner known per se, for example by extraction and, if appropriate, further chemical or physical purification processes such as, for example, precipitation methods, crystallography, thermal separation methods like rectification methods or physical separation methods such as, for example, chromatography.

The invention furthermore relates to a method for generating a genetically modified organism in which, starting from a starting organism, the Δ22-desaturase activity is reduced and the HMG-CoA reductase activity is increased and at least one of the activities selected from the group consisting of lanosterol C14-demethylase activity, squalene epoxidase activity and squalene synthetase activity is increased.

The methods for deleting the target locus Δ22-desaturase gene have already been detailed above.

The transgenic organisms, in particular yeasts, can preferably be generated by transforming the starting organisms, in particular yeasts, with a nucleic acid construct comprising at least one nucleic acid encoding an HMG-CoA reductase and comprising at least one nucleic acid selected from the group consisting of nucleic acids encoding a lanosterol C14-demethylase, nucleic acids encoding a squalene epoxidase and nucleic acids encoding a squalene synthetase, which nucleic acids are linked operably to one or more regulatory signals which ensure the transcription and translation in the organisms. In this embodiment, the transgenic organisms are generated using a nucleic acid construct.

Nucleic acid constructs which can be used for this purpose are those which, in addition to the expression cassettes described hereinbelow and comprising promoter, coding sequence and, if appropriate, terminator, and in addition to a selection marker described hereinbelow, comprise, at their 3' and 5' ends, nucleic acid sequences which are identical to nucleic acid sequences at the beginning and at the end of the gene to be deleted.

However, the transgenic organisms may also preferably be generated by transforming the starting organisms, in particular yeasts, with a combination of nucleic acid constructs comprising nucleic acid constructs comprising at least one nucleic acid encoding an HMG-CoA reductase and comprising nucleic acid constructs or a combination of nucleic acid constructs comprising at least one nucleic acid selected from the group consisting of nucleic acids encoding a lanosterol C14-demethylase, nucleic acids encoding a squalene epoxidase and nucleic acids encoding a squalene synthetase and which are in each case linked operably to one or more regulatory signals which ensure the transcription and translation in organisms.

In this embodiment, the transgenic organisms are generated using individual nucleic acid constructs or a combination of nucleic acid constructs.

Nucleic acid constructs in which the coding nucleic acid sequence is linked operably to one or more regulatory signals which ensure the transcription and translation in organisms, in particular in yeasts, are hereinbelow also referred to as expression cassettes.

Nucleic acid constructs comprising this expression cassette are, for example, vectors or plasmids.

The regulatory signals preferably comprise one or more promoters which ensure the transcription and translation in organisms, in particular in yeasts.

The expression cassettes comprise regulatory signals, that is to say regulatory nucleic acid sequences which control the expression of the coding sequence in the host cell. In accordance with a preferred embodiment, an expression cassette encompasses a promoter upstream, i.e. at the 5' end of the coding sequence, and a terminator downstream, i.e. at the 3' end, and, if appropriate, further regulatory elements which are linked operably to the interposed coding sequence for at least one of the above-described genes.

Operable linkage is understood as meaning the sequential arrangement of promoter, coding sequence, if appropriate terminator and if appropriate further regulatory elements in such a way that each of the regulatory elements can fulfill its intended function upon expression of the coding sequence.

By way of example, the preferred nucleic acid constructs, expression cassettes and plasmids for yeasts and fungi and methods for generating transgenic yeasts and the transgenic yeasts themselves are described in the following text.

A suitable promoter for the expression cassette is, in principle, any promoter which is capable of controlling the expression of foreign genes in organisms, in particular in yeasts.

A promoter which is preferably used is, in particular, a promoter which is subject to reduced regulation in yeast, such as, for example, the middle ADH promoter.

This promoter fragment of the ADH12s promoter, hereinbelow also referred to as ADH1, shows approximately constitutive expression (Ruohonen L, Penttila M, Keranen S. (1991) Optimization of *Bacillus* alpha-amylase production by *Saccharomyces cerevisiae*. Yeast. May-June; 7(4):337-462; Lang C, Looman A C. (1995) Efficient expression and secretion of *Aspergillus niger* RH5344 polygalacturonase in *Saccharomyces cerevisiae*. Appl Microbiol Biotechnol. December; 44(1-2):147-56.), so that transcriptional regulation is no longer effected by ergosterol biosynthesis intermediates.

Further preferred promoters with reduced regulation are constitutive promoters such as, for example, the yeast TEF1 promoter, the yeast GPD promoter or the yeast PGK promoter (Mumberg D, Muller R, Funk M. (1995) Yeast vectors for the controlled expression of heterologous proteins in different genetic backgrounds. Gene. 1995 Apr. 14; 156(1):119-22; Chen C Y, Oppermann H, Hitzeman R A. (1984) Homologous versus heterologous gene expression in the yeast, *Saccharomyces cerevisiae*. Nucleic Acids Res. December 11; 12(23): 8951-70.).

The expression cassette may also comprise inducible promoters, in particular chemically inducible promoters, by means of which the expression, in the organism, of the nucleic acids encoding an HMG-CoA reductase, lanosterol C14-demethylase, squalene epoxidase or squalene synthetase can be controlled at a particular point in time.

Such promoters such as, for example, the yeast Cupl promoter, (Etcheverry T. (1990) Induced expression using yeast copper metallothionein promoter. Methods Enzymol. 1990; 185:319-29.), the yeast Gal1-10 promoter (Ronicke V, Graulich W, Mumberg D, Muller R, Funk M. (1997) Use of conditional promoters for expression of heterologous proteins in *Saccharomyces cerevisiae*, Methods Enzymol. 283:313-22) or the yeast Pho5 promoter (Bajwa W, Rudolph H, Hinnen A. (1987) PHO5 upstream sequences confer phosphate control on the constitutive PHO3 gene. Yeast. 1987 March; 3(1):33-42) may be used by way of example.

A suitable terminator for the expression cassette is, in principle, any terminator which is capable of controlling the expression of foreign genes in organisms, in particular in yeasts.

The yeast tryptophan terminator (TRP1 terminator) is preferred.

An expression cassette is preferably generated by fusing a suitable promoter to the above-described nucleic acids encoding an HMG-CoA reductase, lanosterol C14-demethylase, squalene epoxidase or squalene synthetase and, if appropriate, a terminator using customary recombination and cloning techniques as are described, for example, in T. Maniatis, E. F. Fritsch and J. Sambrook, Molecular Cloning: A Laboratory Manual, Cold Spring Harbor Laboratory, Cold Spring Harbor, N.Y. (1989), in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

The nucleic acids according to the invention can have been synthesized or obtained naturally or comprise a mixture of synthetic and natural nucleic acid components, or else consist of various heterologous gene segments from various organisms.

Preferred are, as described above, synthetic nucleotide sequences with codons which are preferred by yeasts. These codons which are preferred by yeasts can be determined from codons with the highest protein frequency which are expressed in most of the yeast species of interest.

When preparing an expression cassette, various DNA fragments can be manipulated in order to obtain a nucleotide sequence which expediently reads in the correct direction and is equipped with the correct reading frame. Adapters or linkers may be added to the fragments in order to link the DNA fragments with one another.

The promoter and terminator regions may expediently be provided, in the direction of transcription, with a linker or polylinker comprising one or more restriction cleavage sites for the insertion of this sequence. As a rule, the linker has 1 to 10, in most cases 1 to 8, preferably 2 to 6, restriction cleavage sites. In general, the linker within the regulatory regions has a size of less than 100 bp, frequently less than 60 bp, but at least 5 bp. The promoter may be either native, or homologous, or else foreign, or heterologous, with respect to the host organism. The expression cassette preferably comprises, in the 5'-3' direction of transcription, the promoter, a coding nucleic acid sequence or a nucleic acid construct and a region for transcriptional termination. Various termination regions can be exchanged for one another as desired.

Manipulations which provide suitable restriction cleavage sites or which remove superfluous DNA or restriction cleavage sites may furthermore be employed. Where insertions, deletions or substitutions such as, for example, transitions and transversions, are suitable, in vitro mutagenesis, primer repair, restriction or ligation may be used.

Suitable manipulations such as, for example, restriction, chewing back or filling in overhangs for blunt ends may provide complementary ends of the fragments for the ligation.

The invention furthermore relates to the use of the above-described nucleic acids, the above-described nucleic acid constructs or the above-described proteins for the generation of transgenic organisms, in particular yeasts.

These transgenic organisms, in particular yeasts, preferably have an increased content in ergosta-5,7-dienol and/or its biosynthetic intermediates and/or metabolites in comparison with the wild type.

The invention furthermore relates to the use of the above-described nucleic acids or of the nucleic acid constructs according to the invention for increasing the content in ergosta-5,7-dienol and/or its biosynthetic intermediates and/or metabolites in organisms.

The above-described proteins and nucleic acids can be used for producing ergosta-5,7-dienol and/or its biosynthetic intermediates and/or metabolites in transgenic organisms.

The transfer of foreign genes into the genome of an organism, in particular of yeast, is referred to as transformation.

Transformation methods which are known per se may be used for this purpose, in particular in yeasts.

Suitable methods for transforming yeasts are, for example, the LiAC method as described in Schiestl R H, Gietz R D. (1989) High efficiency transformation of intact yeast cells using single stranded nucleic acids as a carrier, Curr Genet. December; 16(5-6):339-46, the electroporation as described in Manivasakam P, Schiestl R H. (1993) High efficiency transformation of Saccharomyces cerevisiae by electroporation. Nucleic Acids Res. September 11; 21(18):4414-5, or the preparation of protoplasts as described in Morgan A J. (1983) Yeast strain improvement by protoplast fusion and transformation, Experientia Suppl. 46:155-66.

The construct to be expressed is preferably cloned into a vector, in particular into plasmids which are suitable for the transformation of yeasts, such as, for example, the vector systems Yep24 (Naumovski L, Friedberg E C (1982) Molecular cloning of eucaryotic genes required for excision repair of UV-irradiated DNA: isolation and partial characterization of the RAD3 gene of Saccharomyces cerevisiae. J Bacteriol October; 152(1):323-31), Yep13 (Broach J R, Strathern J N, Hicks J B. (1979) Transformation in yeast: development of a hybrid cloning vector and isolation of the CAN1 gene. Gene. 1979 December; 8(1):121-33), the pRS vector series (Centromer and Episomal) (Sikorski R S, Hieter P. (1989) A system of shuttle vectors and yeast host strains designed for efficient manipulation of DNA in Saccharomyces cerevisiae. Genetics. May; 122(1):19-27) and the vector systems YCp19 or pYEXBX.

Accordingly, the invention furthermore relates to vectors, in particular plasmids comprising the above-described nucleic acids, nucleic acid constructs or expression cassettes.

The invention furthermore relates to a method for the generation of genetically modified organisms by functionally inserting, into the starting organism, an above-described nucleic acid or an above-described nucleic acid construct.

The invention furthermore relates to the genetically modified organisms, where the genetic modification reduces the Δ22-desaturase activity and increases the HMG-CoA reductase activity and increases at least one of the activities selected from the group consisting of lanosterol C14-demethylase activity, squalene epoxidase activity and squalene synthetase activity in comparison with the wild type.

In a preferred embodiment, the genetically modified organisms have a reduced Δ22-desaturase activity and an increased HMG-CoA reductase activity and an increased lanosterol C14-demethylase activity in comparison with the wild type.

In a further preferred embodiment, the genetically modified organisms have a reduced Δ22-desaturase activity and an increased HMG-CoA reductase activity and an increased squalene epoxidase activity in comparison with the wild type.

In a further preferred embodiment, the genetically modified organisms have a reduced Δ22-desaturase activity and an increased HMG-CoA reductase activity and an increased squalene synthetase activity in comparison with the wild type.

In an especially preferred embodiment, the genetically modified organisms have a reduced Δ22-desaturase activity and an increased HMG-CoA reductase activity and an increased lanosterol C14-demethylase activity and an increased squalene epoxidase activity in comparison with the wild type.

In a further, especially preferred embodiment, the genetically modified organisms have a reduced Δ22-desaturase activity and an increased HMG-CoA reductase activity and an increased lanosterol C14-demethylase activity and an increased squalene synthetase activity in comparison with the wild type.

In a further, especially preferred embodiment, the genetically modified organisms have a reduced Δ22-desaturase activity and an increased HMG-CoA reductase activity and an increased squalene epoxidase activity and an increased squalene synthetase activity in comparison with the wild type.

In a very especially preferred embodiment, the genetically modified organisms have a reduced Δ22-desaturase activity and an increased HMG-CoA reductase activity and an increased lanosterol C14-demethylase activity and an increased squalene epoxidase activity and an increased squalene synthetase activity in comparison with the wild type.

As mentioned above, these activities are preferably increased by increasing independently, in comparison with the wild type, the gene expression of nucleic acids encoding an HMG-CoA reductase, nucleic acids encoding a lanosterol C14-demethylase, nucleic acids encoding a squalene epoxidase or nucleic acids encoding a squalene synthetase.

The furthermore preferred embodiments of the preferred genetically modified organisms according to the invention are described hereinabove in the methods.

The above-described genetically modified organisms have an increased content in ergosta-5,7-dienol and/or its biosynthetic intermediates and/or metabolites in comparison with the wild type.

Accordingly, the invention relates to an above-described genetically modified organism, wherein the genetically modified organism has an increased content in ergosta-5,7-dienol and/or its biosynthetic intermediates and/or metabolites in comparison with the wild type.

Organisms or genetically modified organisms are understood as meaning, in accordance with the invention, for example bacteria, in particular bacteria of the genus *Bacillus, Escherichia coli, Lactobacillus* spec. or *Streptomyces* spec., for example yeasts, in particular yeasts of the genus *Saccharomyces cerevisiae, Pichia pastoris* or *Klyveromyces* spec., for example fungi, in particular fungi of the genus *Aspergillus* spec., *Penicillium* spec. or *Dictyostelium* spec., and, for example, also insect cell lines which are capable of generating ergosta-5,7-dienol and/or its biosynthetic intermediates and/or metabolites, either as the wild type or owing to preceding genetic modification.

Especially preferred organisms or genetically modified organisms are yeasts, in particular of the species *Saccharomyces cerevisiae*, in particular the yeast strains *Saccharomyces cerevisiae* AH22, *Saccharomyces cerevisiae* GRF, *Saccharomyces cerevisiae* DBY747 and *Saccharomyces cerevisiae* BY4741.

Increasing the content in ergosta-5,7-dienol and/or its biosynthetic intermediates and/or metabolites means, for the purposes of the present invention, preferably the artificially acquired ability of an increased biosynthesis rate of at least one of these compounds mentioned at the outset in the genetically modified organism in comparison with the non-genetically-modified organism.

An increased content in ergosta-5,7-dienol and/or its biosynthetic intermediates and/or metabolites in comparison with the wild type is understood as meaning in particular increasing the content of at least one of the abovementioned compounds in the organism by at least 50%, by preference 100%, more preferably 200%, especially preferably 400% in comparison with the wild type.

The determination of the content in at least one of the abovementioned compounds is preferably carried out by analytical methods known per se and preferably relates to those compartments of the organism in which sterols are produced.

The advantage of the present invention in comparison with the prior art is as follows:

The method according to the invention makes it possible to increase the content in ergosta-5,7-dienol and/or its biosynthetic intermediates and/or metabolites in the production organisms.

The invention will now be illustrated by the examples which follow, but is not limited thereto:

I. General Experimental Conditions

1. Restriction

The plasmids (1 to 10 μg) were restricted in 30 μl reactions. To this end, the DNA was taken up in 24 μl of $H_2O$ and treated with 3 μof the buffer in question, 1 ml of BSA (bovine serum albumin) and 2 μl of enzyme. The enzyme concentration was 1 unit/μl or 5 units/μl, depending on the DNA quantity. In some cases, 1 μl of RNase was also added to the reaction in order to break down the tRNA. The restriction reaction was incubated for 2 hours at 37° C. The restriction was checked with a minigel.

2. Gel Electrophoreses

The gel electrophoreses were carried out in minigel or wide minigel apparatuses. The minigels (approx. 20 ml, 8 wells) and the wide minigels (50 ml, 15 or 30 wells) consisted of 1% agarose in TAE. The running buffer used was 1× TAE. The samples (10 μl) were treated with 3 μl of stop solution and applied. HindIII-cut I-DNA acted as the standard (bands at: 23.1 kb; 9.4 kb; 6.6 kb; 4.4 kb; 2.3 kb; 2.0 kb; 0.6 kb). For the separation, 80 volts were applied for 45 to 60 minutes. Thereafter, the gel was stained in ethidium bromide solution and, under UV light, recorded with the video documentation system INTAS or photographed using an orange filter.

3. Gel Elution

The desired fragments were isolated by means of gel elution. The restriction reaction was loaded into several wells of a minigel and run. Only λ-HindIII and a "sacrificial lane" were stained with ethidium bromide solution and viewed under UV light, and the desired fragment was marked. Damage by the ethidium bromide and the UV light to the DNA in the remaining wells was thus prevented. By placing the stained and the unstained gel slab next to each other, it was possible to excise the desired fragment from the unstained gel slab with reference to the marker. The agarose section with the fragment to be isolated was placed into a dialysis tube, sealed with a small amount of TAE buffer without air bubbles and placed into the BioRad minigel apparatus. The running buffer consisted of 1× TAE, and the voltage applied was 100 V for 40 minutes. Thereafter, the polarity of the current was reversed for 2 minutes in order to redissolve the DNA which stuck to the dialysis tube. The buffer, of the dialysis tube, which contained the DNA fragments was transferred into reaction vessels and used for carrying out an ethanol precipitation. To this end, 1/10 volume of 3M sodium acetate, tRNA (1 µl per 50 µl solution) and 2.5 volumes of ice-cold 96% ethanol were added to the DNA solution. The reaction was incubated for 30 minutes at −20° C. and then centrifuged for 30 minutes at 4° C. at 12 000 rpm. The DNA pellet was dried and taken up in 10 to 50 µl of $H_2O$ (depending on the DNA quantity).

4. Klenow Treatment

The Klenow treatment results in DNA fragment overhangs being filled in so that blunt ends result. The following mixture was pipetted together for each µg of DNA:

DNA pellet+11 µl H20
+1.5 µl 10× Klenow buffer
+1 µl 0.1 M DTT
+1 µl nucleotide (dNTP 2 mM)
25+1 µl Klenow polymerase (1 unit/µl)

The DNA for this purpose should originate from an ethanol precipitation in order to prevent contaminants inhibiting the Klenow polymerase. The mixture was incubated for 30 minutes at 37° C. and the reaction was stopped by a further 5 minutes at 70° C. The DNA was obtained from the mixture by precipitation of ethanol and taken up in 10 µl of $H_2O$.

5. Ligation

The DNA fragments to be ligated were combined. The final volume of 13.1 µl contained approx. 0.5 µl of DNA with a vector:insert ratio of 1:5. The sample was incubated for 45 seconds at 70° C., cooled to room temperature (approx. 3 minutes) and then incubated for 10 minutes on ice. Thereafter, the ligation buffers were added: 2.6 µl 500 mM trisHCl pH 7.5 and 1.3 µl 100 mM $MgCl_2$, and the mixture was incubated on ice for a further 10 minutes. After addition of 1 µl 500 mM DTT and 1 µl 10 mM ATP and another 10 minutes on ice, 1 µl of ligase (1 unit/pl) was added. The whole of the treatment should be carried out as free from vibrations as possible in order not to separate joined-up DNA ends again. The ligation was carried out overnight at 14° C.

6. E. coli Transformation

Competent *Escherichia coli* (*E. coli*) NM522 cells were transformed with the DNA of the ligation reaction. This was accompanied by a reaction with 50 µg of the pScL3 plasmid as positive control and a reaction without DNA as zero control. For each transformation reaction, 100 µl of 8% PEG solution, 10 µl of DNA and 200 µl of competent cells (*E. coli* NM522) were pipetted into a tabletop centrifuge tube. The reactions were placed on ice for 30 minutes and shaken occasionally.

They were then given the thermal shock treatment: 1 minute at 42° C. For the regeneration, 1 ml of LB medium was added to the cells and the mixtures were incubated for 90 minutes at 37° C. on a shaker. 100 µl portions of the undiluted reactions, of a 1:10 dilution and of a 1:100 dilution were plated onto LB+ ampicillin plates and incubated overnight at 37° C.

7. Plasmid Isolation from E. coli (Miniprep)

*E. coli* colonies were grown overnight in 1.5 ml of LB+ ampicillin medium in tabletop centrifuge tubes at 37° C. and 120 rpm. On the next day, the cells were centrifuged for 5 minutes at 5000 rpm and 4° C. and the pellet was taken up in 50 µl of TE buffer. Each reaction was treated with 100 µl of 0.2 N NaOH, 1% SDS solution, mixed and placed on ice for 5 minutes (cell lysis). Thereafter, 400 µl of sodium acetate/NaCl solution (230 µl of $H_2O$, 130 µl of 3 M sodium acetate, 40 µl of 5M NaCl) were added, the reaction was mixed and placed on ice for a further 15 minutes (protein precipitation). After centrifugation for 15 minutes at 11 000 rpm, the supernatant, which contains the plasmid DNA, was transferred into an Eppendorf tube. If the supernatant was not entirely clear, it was recentrifuged. The supernatant was treated with 360 µl of ice-cold isopropanol and incubated for 30 minutes at −20° C. (DNA precipitation). The DNA was centrifuged off (15 min, 12 000 rpm, 4° C.), the supernatant was discarded, and the pellet was washed in 100 µl of ice-cold 96% ethanol, incubated for 15 minutes at −20° C. and recentrifuged (15 min, 12 000 rpm, 4° C.). The pellet was dried in a SpeedVac apparatus and then taken up in 100 µl of $H_2O$. The plasmid DNA was characterized by restriction analysis. To this end, 10 µl of each reaction were restricted and separated by gel electrophoresis in a wide minigel (see above).

8. Plasmid Preparation from E. coli (Maxiprep)

In order to isolate larger amounts of plasmid DNA, the maxiprep method was carried out. Two flasks containing 100 ml of LB+ ampicillin medium were inoculated with a colony or with 100 µl of a frozen culture containing the plasmid to be isolated and incubated overnight at 37° C. and 120 rpm. On the next day, the culture (200 ml) was transferred into a GSA beaker and centrifuged for 10 minutes at 4000 rpm (2600×g). The cell pellet was taken up in 6 ml of TE buffer. To digest the cell wall, 1.2 ml of lysozyme solution (20 mg/ml TE buffer) were added and the mixture was incubated for 10 minutes at room temperature. The cells were subsequently lysed with 12 ml of 0.2 N NaOH, 1% SDS solution and a further 5 minutes' incubation at room temperature; The proteins were precipitated by addition of 9 ml of cold 3 M sodium acetate solution (pH 4.8) and 15 minutes' incubation on ice. After the centrifugation (GSA: 13 000 rpm (27 500×g), 20 min, 4° C.), the supernatant, which contained the DNA, was transferred into a fresh GSA beaker and the DNA was precipitated with 15 ml of ice-cold isopropanol and 30 minutes' incubation at −20° C. The DNA pellet was washed in 5 ml of ice-cold ethanol and dried in the air (approx. 30-60 min). It was then taken up in 1 ml of $H_2O$. The plasmid was verified by restriction analysis. The concentration was determined by applying dilutions to a minigel. A microdialysis (pore size 0.025 µm) was carried out for 30-60 minutes in order to reduce the salt content.

9. Yeast Transformation

A preculture of the strain *Saccharomyces cerevisiae* AH22 was established for the yeast transformation. A flask containing 20 ml of YE medium was inoculated with 100 µl of the frozen culture and incubated overnight at 28° C. and 120 rpm. The main culture was carried out under identical conditions in flasks containing 100 ml of YE medium which had been inoculated with 10 µl, 20 µl or 50 µl of the preculture.

9.1 Generation of Competent Cells

On the next day, the flasks were counted using a hematocytometer and the flask with a cell concentration of $3-5 \times 10^7$ cells/ml was chosen for the following procedure. The cells were harvested by centrifugation (GSA: 5000 rpm (4000×g) 10 min). The cell pellet was taken up in 10 ml of TE buffer and divided between two tabletop centrifuge tubes (5 ml each). The cells were centrifuged off for 3 minutes at 6000 rpm and washed twice with in each case 5 ml of TE buffer. The cell pellet was subsequently taken up in 330 µl of lithium acetate buffer per $10^9$ cells, transferred into a sterile 50 ml Erlenmeyer flask and shaken for one hour at 28° C. The cells were thus competent for the transformation.

9.2 Transformation

For each transformation reaction, 15 µl of herring sperm DNA (10 mg/ml), 10 µl of DNA to be transformed (approx 0.5 µg) and 330 µl of competent cells were pipetted into a tabletop centrifuge tube and incubated for 30 minutes at 28° C. (without shaking). Thereafter, 700 µl 50% PEG 6000 were added and the reactions were incubated for a further hour at 28° C. without shaking. This was followed by 5 minutes' heat shock treatment at 42° C. 100 µl of the suspension were plated onto selection medium (YNB, Difco) in order to select for leucine prototrophism. In the case of selection of G418 resistance, the cells are regenerated following the heat shock treatment (see 9.3, regeneration phase).

9.3 Regeneration Phase

Since the selection marker is the resistance to G418, the cells required time for expressing the resistance gene. The transformation reactions were treated with 4 ml of YE medium and incubated overnight at 28° C. on a shaker (120 rpm). On the next day, the cells were centrifuged off (6000 rpm, 3 min), taken up in 1 ml of YE medium, and 100 µl or 200 µl of this were plated onto YE+G418 plates. The plates were incubated for several days at 28° C.

10. Reaction Conditions for the PCR

The reaction conditions for the polymerase chain reaction must be optimized for each individual case and are not generally valid for each procedure. It is thus possible to vary, inter alia, the amount of DNA employed, the salt concentrations and the melting point. For our approach, it proved suitable to combine the following substances in an Eppendorf tube suitable for use in thermocyclers: 5 µl of Super Buffer, 8 µl of dNTPs (0.625 µM each), 5'-primer, 3'-primer and 0.2 µg of template DNA, dissolved in such an amount of water that a total volume of 50 µl for the PCR reaction results, were added to 2 µl (=0.1 U) Super Taq polymerase. The reaction was centrifuged briefly and covered with a drop of oil. Between 37 and 40 cycles were selected for the amplification.

II. EXAMPLES

Example 1

Expression of a Truncated HMG-CoA Reductase in *S. cerevisiae* GRF

The coding nucleic acid sequence for the expression cassette consisting of ADH-promoter-tHMG-tryptophan-terminator was amplified from the vector YepH2 (Polakowski et al. (1998) Overexpression of a cytosolic hydroxymethylglutaryl-CoA reductase leads to squalene accumulation in yeast. Appl Microbiol Biotechnol. January; 49(1):66-71) by PCR using standard methods as detailed above under the general reaction conditions.

The primers used for this purpose are the DNA oligomers AtHT-5' (forward: tHMGNotF: 5'-CTGCGGCCGCAT-CATGGACCMTTGGTGAAAACTG-3'; SEQ. ID. NO. 11) and AtHT-3' (reverse: tHMGXhoR: 5'-MCTCGAGAGACA-CATGGTGCTGTTGTGCTTC-3'; SEQ. ID. No. 12).

The resulting DNA fragment was first treated with Klenow and then cloned blunt-ended into the vector, pUG6 into the EcoRV cleavage site, giving rise to the vector pUG6-tHMG (FIG. 1).

Following the isolation of the plasmid, an extended fragment was amplified from the vector pUG-tHMG by means of PCR so that the resulting fragment consists of the following components: loxP-kanMX-ADH-promoter-tHMG-tryptophan-terminator-loxP. The primers chosen were oligonucleotide sequences which, at the 5' and 3' overhangs, comprise the 5' or the 3' sequence of the URA3 gene, respectively, and in the annealing region the sequences of the loxP regions 5' and 3' of the vector pUG-tHMG. This ensures that firstly the entire fragment including KanR and tHMG is amplified and secondly that this fragment can subsequently be transformed into yeast and the entire fragment integrates into the yeast URA3 gene locus by homologous recombination.

The selection marker used is the resistance to G418. The resulting strain *S. cerevisiae* GRF-tH1ura3 is Uracil-auxotrophic and contains a copy of the gene tHMG under the control of the ADH promoter and tryptophan terminator.

In order to subsequently remove the resistance to G418 again, the resulting yeast strain is transformed with the cre recombinase vector pSH47 (Guldener U, Heck S, Fielder T, Beinhauer J, Hegemann J H. (1996) A new efficient gene disruption cassette for repeated use in budding yeast. Nucleic Acids Res. July 1; 24(13):2519-24.). Owing to this vector, the cre recombinase is expressed in the yeast, and, as a consequence, the sequence region within the two loxP sequences recombines out of the gene. The result is that only one of the two loxP sequences and the ADH-tHMG-TRP cassette are retained in the URA3 gene locus. As a consequence, the yeast strain loses the G418 resistance again and is thus suitable for integrating further genes into the yeast strain by means of this cre-lox system or removing them, respectively. The vector pSH47 can now be removed again by counterselection on YNB agar plates supplemented with Uracil (20 mg/l) and FOA (5-fluoroorotic acid) (1 g/l). To this end, the cells which bear this plasmid must first be cultured under nonselective conditions and subsequently be grown on FOA-containing selective plates. Only those cells which are not capable of synthesizing Uracil themselves are capable of growing under these conditions. In the present case, these are cells which no longer contain plasmid (pSH47).

The yeast strain GRFtH 1 ura3 and the original strain GRF were cultured for 48 hours in WMXIII medium at 28° C. and 160 rpm in a culture volume of 20 ml. 500 µl of this preculture were subsequently transferred into a 50 ml main culture of the same medium and cultured for 4 days at 28° C. and 160 rpm in a baffle flask.

The sterols were extracted after 4 days following the method as described in Parks L W, Bottema C D, Rodriguez R J, Lewis T A. (1985) Yeast sterols: yeast mutants as tools for the study of sterol metabolism. Methods Enzymol. 1985; 111:333-46 and analyzed by gas chromatography. This gives the data listed in table 1. The percentages are based on the yeast dry weight.

TABLE 1

| Sterol content [peak area/gDM] | *S. cerevisiae* GRFtH1ura3 | *S. cerevisiae* GRF |
|---|---|---|
| Squalene | 9.93 | 0.1 |
| Lanosterol | 0.83 | 0.31 |
| Zymosterol | 1.18 | 1.07 |
| Fecosterol | 1.10 | 0.64 |
| Episterol/ergosta-5,7-dienol | 1.04 | 0.72 |
| Dimethyl-zymosterol | 0.34 | 0.13 |

Example 2

Expression of ERG1 in *S. cerevisiae* GRFtH1ura3 with Simultaneous Deletion of ERG5; Generation of GRFtH1ura3ERG1erg5

Example 2.1

Generation of the Integration Vector pUG6-ERG1

Figure 2:
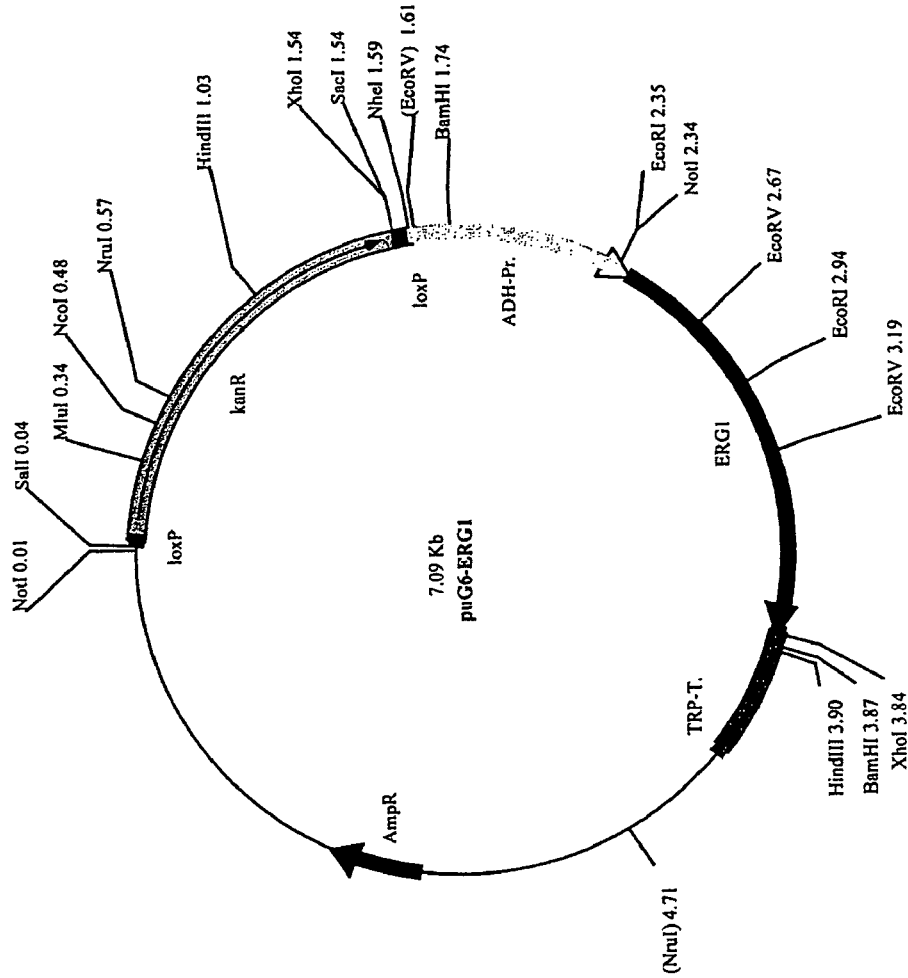
FIG. 2 shows vector pUG6 ERG1.

The DNA sequence for the cassette consisting of ADH-promoter-ERG1-tryptophan-terminator was isolated from the vector pFlat3-ERG1 by restriction with the enzymes NheI and Bsp68l(NruI) using standard methods. The resulting DNA fragment was treated with Klenow and then cloned blunt-ended into the vector pUG6 into the EcoRV cleavage site, giving rise to the vector pUG6-ERG1 (FIG. 2).

Example 2.2.

Integrative Transformations

Following the isolation of the plasmid, an extended fragment was amplified from the vector pUG6-ERG1 by means of PCR so that the resulting fragment consists of the following components: loxP-kanMX-loxP-ADH1-Pr.-ERG1-Trp-Term. The primers used were oligonucleotide sequences which contain, in the annealing region, the sequences beyond the cassette to be amplified, of the vector pUG6-ERG1, and at the 5' and 3' overhangs the 5' or the 3' sequence of the integration locus ERG5, respectively. This ensures that firstly the entire fragment including KanR and the target gene ERG1 is amplified and secondly that this fragment can subsequently be transformed into yeast and integrates into the yeast target gene locus ERG5 by homologous recombination. The following primers were used for this purpose:

```
ERG5-Crelox-5' (SEQ ID NO: 13):
5'-ATGAGTTCTG TCGCAGAAAA TATAATACAA CATGCCACTC
CCAGCTGAAGCTTCGTACGC-3'
and ERG5-Crelox-3' (SEQ ID NO: 14):
5'-TTATTCGAAG ACTTCTCCAG TAATTGGGTC TCTCTTTTTG
GCATAGGCCA CTAGTGGATC TG-3'
```

The selection marker used is the resistance to geneticin (G418). The resulting strain contains one copy of the target gene ERG1 under the control of the ADH1 promoter and the tryptophan terminator. By integration of the gene it is simultaneously possible to delete the corresponding gene ERG5 of the target locus. In order to subsequently remove the resistance to G418 again, the resulting yeast strain is transformed with the cre recombinase vector pSH47. Owing to this vector, the cre recombinase is expressed in the yeast, and, as a consequence, the sequence region within the two loxP sequences recombines out of the gene, the result of which is that only one of the two loxP sequences and the cassette consisting of ADH1-prom.-ERG1-TRP1-term. are retained in the target locus ERG5. As a consequence, the yeast strain loses the G418 resistance again. The vector pSH47 can now be removed selectively by cultivation on FOA medium.

The resulting yeast strain GRFtH1ura3ERG1erg5 was cultured for 48 hours in WMVII medium at 28° C. and 160 rpm in a culture volume of 20 ml. 500 µl of this preculture were subsequently transferred into a 50 ml main culture of the same medium and cultured for 3 days at 28° C. and 160 rpm in a baffle flask.

The sterols were extracted after 4 days following the method as described in Parks L W, Bottema C D, Rodriguez R J, Lewis T A. (1985) Yeast sterols: yeast mutants as tools for the study of sterol metabolism. Methods Enzymol. 1985; 111:333-46 and analyzed by gas chromatography. This gives the data listed in table 2. The percentages are based on the yeast dry weight.

TABLE 2

| Sterol content [peak area/gDM] | S. cerevisiae GRFtH1ura3ERG1erg5 | S. cerevisiae GRF |
|---|---|---|
| Squalene | 8.1 | 0.1 |
| Lanosterol | 2.42 | 0.31 |
| Zymosterol | 1.35 | 1.07 |
| Fecosterol | 2.01 | 0.64 |
| Episterol/ergosta-5,7-dienol | 12.21 | 0.72 |
| Dimethyl-zymosterol | 1.02 | 0.13 |

Comparative Example 1

Deletion of ERG5 in S. cerevisiae GRFtH1ura3; Generation of GRFtH1ura3erg5

The deletion of ERG5 in S. cerevisiae GRFtH1ura3 was carried out analogously to example 2. In order to delete only the ERG5 gene, the same method was used, but the vector pUG6 was employed instead of the vector pUG6-ERG1. This vector pUG6 contains no cassette consisting of ADH-prom-ERG1-Trp-term. By using this vector, it is possible to delete one gene, in this case the gene ERG5.

The resulting yeast strain GRFtH1 ura3erg5 was cultured for 48 hours in WMVII medium at 28° C. and 160 rpm in a culture volume of 20 ml. 500 µl of this preculture were subsequently transferred into a 50 ml main culture of the same medium and cultured for 3 days at 28° C. and 160 rpm in a baffle flask.

The sterols were extracted after 4 days following the method as described in Parks L W, Bottema C D, Rodriguez R J, Lewis T A. (1985) Yeast sterols: yeast mutants as tools for the study of sterol metabolism. Methods Enzymol. 1985; 111:333-46 and analyzed by gas chromatography. This gives the data listed in table 3. The percentages are based on the yeast dry weight.

TABLE 3

| Sterol content [peak area/g DM] | GRFtH1ura3ERG1erg5 (Example 2) | GRFtH1ura3erg5 (Comparative example) |
|---|---|---|
| Squalene | 8.1 | 13.18 |
| Lanosterol | 2.42 | 0.78 |
| Zymosterol | 1.35 | 0.10 |
| Fecosterol | 2.01 | 1.03 |
| Episterol/ergosta-5,7-dienol | 12.21 | 8.98 |
| 4,4-Dimethylzymosterol | 1.02 | 0.21 |

We claim:

1. A method for the production of ergosta-5,7-dienol comprising culturing a genetically modified yeast organism, wherein the genetic modification reduces the Δ22-desaturase activity consisting of the enzymatic activity of Δ22-desaturase having the amino acid sequence of SEQ ID.NO: 2 and increases the HMG-CoA reductase activity consisting of the enzymatic activity of HMG-CoA reductase having the amino acid sequence of SEQ ID.NO: 4 and increases squalene epoxidase activity consisting of the enzymatic activity of squalene epoxidase having the amino acid sequence of SEQ ID.NO: 8 in comparison with the wild type.

2. The method as claimed in claim 1, wherein, in order to reduce the Δ22-desaturase activity, the gene expression of a nucleic acid encoding a Δ22-desaturase is reduced in comparison with the wild type organism.

3. The method as claimed in claim 2, wherein an organism without a functional Δ22-desaturase gene is used.

4. The method as claimed in claim 1, wherein, in order to increase the HMG-CoA reductase activity, the gene expression of a nucleic acid encoding an HMG-CoA reductase is increased in comparison with the wild type organism.

5. The method as claimed in claim 4, wherein, in order to increase gene expression, a nucleic acid construct comprising a nucleic acid encoding an HMG-CoA reductase is introduced into the organism and whose expression in the organism is subject to reduced regulation in comparison with the wild type organism.

6. The method as claimed in claim 5, wherein the nucleic acid construct comprises a promoter which, in the organism, is subject to reduced regulation in comparison with the wild-type promoter.

7. The method as claimed in claim 6, wherein the nucleic acid encoding an HMG-CoA reductase is a nucleic acid whose expression in the organism is subject to reduced regulation in comparison with the homologous, orthologous nucleic acid.

8. The method as claimed in claim 7, wherein the nucleic acid encoding an HMG-CoA reductase is a nucleic acid which encodes the catalytic region of HMG-CoA reductase.

9. The method as claimed in claim 8, wherein the nucleic acids introduced are nucleic acids encoding proteins comprising the amino acid sequence SEQ. ID. NO. 4.

10. The method as claimed in claim 9, wherein a nucleic acid comprising the sequence SEQ. ID. NO. 3 is introduced.

11. The method as claimed in claim 1, wherein, in order to increase the squalene epoxidase activity, the gene expression of a nucleic acid encoding a squalene epoxidase is increased in comparison with the wild type organism.

12. The method as claimed in claim 11, wherein, in order to increase gene expression, one or more nucleic acids encoding a squalene epoxidase are introduced into the organism.

13. The method as claimed in claim 12, wherein the nucleic acids introduced are nucleic acids encoding proteins comprising the amino acid sequence SEQ. ID. NO. 8.

14. The method as claimed in claim 13, wherein a nucleic acid comprising the sequence SEQ. ID. NO. 7 is introduced.

* * * * *